United States Patent [19]

Ashton et al.

[11] Patent Number: 4,816,447

[45] Date of Patent: Mar. 28, 1989

[54] ANTI-VIRAL GUANINE COMPOUNDS

[75] Inventors: Wallace T. Ashton, Clark, N.J.; Arthur K. Field, North Wales, Pa.; John D. Karkas, New York, N.Y.; Richard L. Tolman, Warren, N.J.

[73] Assignee: Merck & Co., Inc., Rahway, N.J.

[21] Appl. No.: 617,868

[22] Filed: Jun. 6, 1984

Related U.S. Application Data

[63] Continuation-in-part of Ser. No. 405,634, Aug. 5, 1982, abandoned, which is a continuation-in-part of Ser. No. 296,604, Aug. 26, 1981, abandoned.

[51] Int. Cl.$^4$ .................... C07D 473/18; A61K 31/52
[52] U.S. Cl. ..................... 514/81; 544/244; 544/276; 544/277
[58] Field of Search ............. 544/276, 277, 244; 424/253; 514/81, 262

[56] References Cited

U.S. PATENT DOCUMENTS

| | | | |
|---|---|---|---|
| 4,199,574 | 4/1980 | Schaeffer | 544/244 |
| 4,287,188 | 9/1981 | Schaeffer | 544/244 |
| 4,590,269 | 5/1986 | Onisbe et al. | 544/277 |
| 4,603,219 | 7/1986 | Verheyden et al. | 544/277 |
| 4,670,424 | 6/1987 | Mac Ross et al. | 514/81 |

*Primary Examiner*—Nicholas S. Rizzo
*Attorney, Agent, or Firm*—Richard S. Parr; Hesna J. Pfeiffer

[57] ABSTRACT 9-(1,3-Dihydroxy-2-propoxymethyl)guanine and 9-(2,3-dihydroxy-1-propoxymethyl)guanine have been found to have potent anti-viral activity against herpes viruses. These compounds, their acyl derivatives, their phosphate derivatives and their pharmaceutically acceptable salts, pharmaceutical formulations containing these compounds, the treatment of DNA viral or herpes viral infections with these compounds, method of preparing these compounds, and novel intermediates useful in their preparation are all disclosed.

The compounds may be prepared by reaction of the appropriate acetoxymethyl ether with diacetylguanine, followed by deprotection. The acetoxymethyl ethers may be obtained by reaction of glycerol formal with acetic anhydride in the presence of a catalyst.

15 Claims, 2 Drawing Sheets

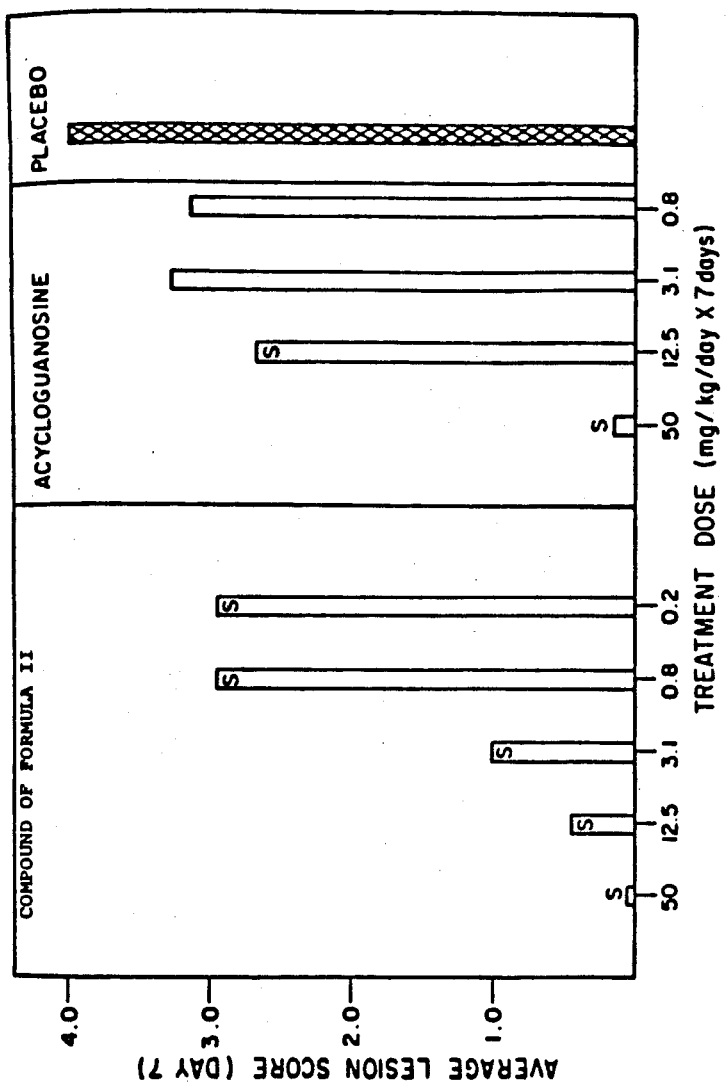

ANTI-VIRAL GUANINE COMPOUNDS

BACKGROUND OF THE INVENTION

This application is a continuation-in-part of U.S. Ser. No. 405,634, filed Aug. 5, 1982, now abandoned which is a continuation-in-part of U.S. Ser. No. 296,604, filed Aug. 26, 1981, now abandoned.

The use of purine derivatives as anti-viral compounds is known. For example, U.S. Pat. No. 4,027,025 discloses 8-azapurine derivatives such as 9-(2-hydroxyethoxymethyl)-8-azaguanine and 9-(2-benzoyloxyethoxymethyl)-8-azaguanine as anti-viral compounds.

U.S. Pat. No. 4,146,715 discloses 2-amido-9-(2-acyloxyethoxymethyl)hypoxanthines.

U.S. Pat. No. 4,199,574 discloses that 9-(2-hydroxyethoxymethyl) and related derivatives of certain 6-, and 2,6-substituted purines have anti-viral activity.

U.S. Pat. Nos. 4,347,360 and 4,355,032 disclose that 9-[[2-hydroxy-1-(hydroxymethyl)ethoxy]methyl]-guanine has anti-viral activity.

Colla et al., *J. Med. Chem.*, 26, 602–604 (1983) disclose esters of acyclovir.

European Patent Application Publication No. 0 095 813 discloses esters and ethers of acyclovir.

European Patent Application Publication No. 0 085 424 sdiscloses acyl derivatives of 9-(1,3-dihydroxy-2-propoxymethyl)guanine.

OBJECTS OF THE INVENTION

It is an object of the present invention to provide novel, anti-viral compounds. Another object of the present invention is to provide novel compounds having enhanced anti-viral activity compared to known anti-viral compounds. Yet another object is to provide compounds having potent anti-viral activity against herpes viruses in general as well as to provide compounds which have utility and safety in the treatment of specific members of the herpes group of virus, such as oral or topical herpes-1 and herpes-2 or topical and systemic agents for life-threatening herpes (for example, cytomegalovirus and varicella zoster). Still another object is to provide compounds having antimycoplasmal activity. A further object of the present invention is to provide pharmaceutical formulations for the effective administration of the novel compounds of the invention. Still another object is to provide methods for the preparation of the novel compounds of the present invention. These and other objects of the present invention will become apparent from the following description.

SUMMARY OF THE INVENTION 9-(1,3-Dihydroxy-2-propoxymethyl)guanine and 9-(2,3-dihydroxy-1-propoxymethyl)guanine and their acyl and phosphate derivatives have been found to have potent anti-viral activities. The first two compounds and their derivatives are particularly effective against herpes type viruses. The compound 9-(1,3-dihydroxy-2-propoxymethyl)guanine cyclic monophosphate is also effective against other DNA viruses, e.g. papilloma viruses. These compounds, and their acyl and phosphate derivatives and their pharmaceutically acceptable salts, pharmaceutical formulations containing these compounds, the treatment of viral infections with these compounds, methods of preparing these compounds, and novel intermediates useful in their preparation are all disclosed. In addition, the acyl derivatives have antimycoplasmal activity.

The compounds of the present invention may be prepared by reaction of the appropriate acetoxymethyl ether with diacetylguanine, followed by deprotection. The acetoxymethyl ethers may be obtained by reaction of glycerol formal with acetic anhydride in the presence of a catalyst.

BRIEF DESCRIPTION OF THE DRAWINGS

FIG. 2 is a bar graph showing results of treating HSV-1 infected mice with acycloguanosine or the compound of formula II.

DETAILED DESCRIPTION

Figure 1:
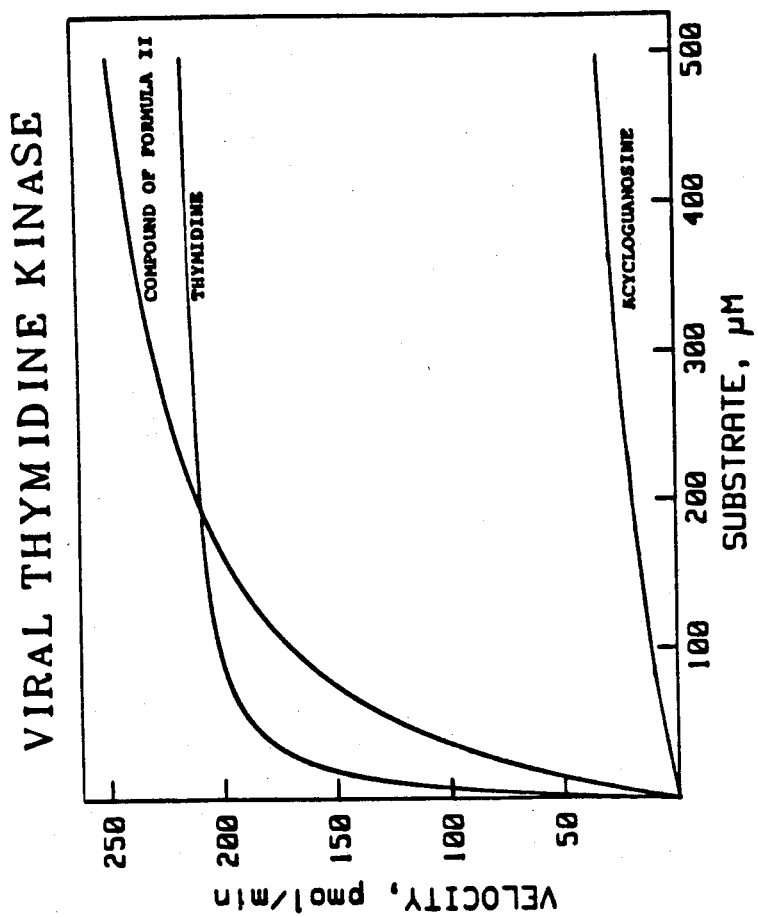
FIG. 1 shows phosphorylation reaction velocity versus concentration curves.

The present invention relates to anti-viral compounds and, more particularly, to 9-(2,3-dihydroxy-1-propoxymethyl)guanine of formula I and 9-(1,3-dihydroxy-2-propoxymethyl)guanine of formula II and to acyl or phosphate derivatives thereof.

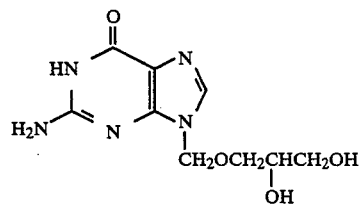

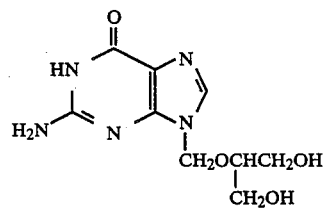

In the compounds of formulas I and II, the hydrogen atom of either hydroxyl group may be replaced by an acyl group. For example, a group of the formula

wherein $R_3$ is a straight or branched chain alkyl group of 1 to 20 carbon atoms which may be saturated or mono- or polyunsaturated, aryl, substituted aryl, heterocyclyl, aralkyl, alkoxyalkyl, or aryloxyalkyl. Also, the hydrogen atom of either hydroxyl group may be substituted by a phosphate group of the formula

or both hydrogens may be replaced by

wherein $R^4$ and $R^5$ are independently H, a pharmaceutically acceptable cation, straight or branched chain alkyl of 1 to 8 carbon atoms, aryl, aralkyl, phosphate or pyrophosphate. In the compound of formula I, when $R_3$ is alkyl, the $R_3$ group may contain one or more hydroxy, amino, or carboxyl groups. Examples of suitable $R_3$ group are $-CH(CH_3)NH_2$, $-CH_2NH_2$, $-CH(CH_2OH)NH_2$, $-(CH_2)_2COOH$, $-CH_2OH$, $-CH(NH_2)CH_2COOH$.

Preferably the alkyl group is from 1 to 10 carbon atoms, the aryl group is phenyl, optionally substituted by halogen or alkyl of 1 to 4 carbon atoms, the heterocyclyl group is pyridyl, piperidyl, furyl, imidazolyl, tetrahydrofuryl or thienyl, the aralkyl group is phenylalkyl wherein the alkyl moiety has 1 to 4 carbon atoms, in the alkoxyalkyl group both the alkoxy and alkyl groups contain 1 to 4 carbon atoms, the aryloxyalkyl group is phenoxyalkyl wherein the alkyl moiety has 1 to 4 carbon atoms, the pharmaceutically acceptable cation is sodium, potassium, ammonium, alkyl substituted ammonium wherein the alkyl moiety has 1 to 4 carbon atoms, magnesium/2, calcium/2, or aluminum/3.

The compounds disclosed herein have biological or chemical properties which give them advantages in the treatment of the various diseases and ailments associated with members of the herpes group of viruses. Specifically, the compound of Formula II and the corresponding cyclic phosphate thereof (hydroxyl hydrogens are replaced by

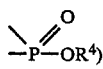

each have major advantages in efficacy and have been shown to operate by independent biological mechanisms. Also, the compound of Formula I is preferred because of its superior safety in use, that is, its lack of genotoxicity which allows it to be used in the treatment of herpes infections of young adults. Furthermore, the corresponding acyl derivatives of the compounds of Formulas I and II are preferred because they have formulation and pharmacodynamic advantages, that is, the acyl group can impart aqueous or oil solubility which is an asset in oral or topical formulation and can facilitate intestinal uptake or passage through the stratum corneum and can also act to extend plasma half-life.

The compounds of formulas I and II may be prepared starting from glycerol formal, a mixture of 1,3-dioxan-5-ol of the formula

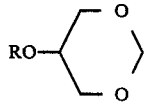

III wherein R is H and 1,3-dioxolane-4-methanol of the formula

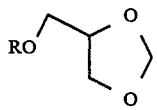

IV wherein R is H, of which the compound of formula III is normally the predominant species. The ratio of compounds of formulas III and IV in glycerol formal has been determined to be 57:43 by H. Tibert, Fresenius' Z. Anal. Chem., 265, 328 (1973). This ratio may vary, however, for different preparations of glycerol formal.

It is to be understood that mixtures containing various ratios of the compounds of formulas III and IV may be employed according to the present invention.

The glycerol formal (mixture of compounds of formulas III and IV) is preferably acylated, e.g. by reaction with an acylating agent such as acetic anhydride in the presence of pyridine, without separation of the individual compounds of formulas III and IV, to give the corresponding acyloxy derivatives wherein R is acyl. This mixture is separated, e.g. by high performance liquid chromatography (HPLC).

Treatment of the compound of formula III wherein R is Ac (acetyl) with acetic anhydride in the presence of a catalyst, e.g. $ZnCl_2$, gives acetoxymethyl 2,3-diacetoxy-1-propyl ether of formula

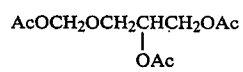

V

This reaction is exothermic and takes place at about ambient temperature preferably in an inert atmosphere, e.g. $N_2$.

The compound of formula V is then purified and reacted neat or in an inert solvent such as triglyme with diacetylguanine, prepared as described by Ishido et al., Bull. Chem. Soc. Japan, 37, 1389 (1964), of the formula

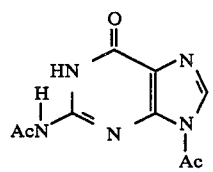

VII at elevated temperature under vacuum in the presence of an acidic catalyst, e.g. ethanesulfonic acid, to form 2-acetamido-9-(2,3-diacetoxy-1-propoxymethyl)hypoxanthine VIII of the formula

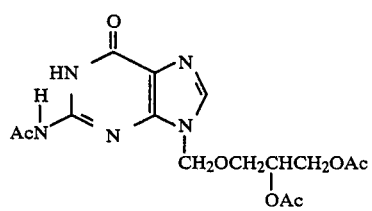

VIII as a viscous oil. The oil is taken up in a suitable solvent, e.g. ethyl acetate, and allowed to crystallize.

The compound of formula VIII is then deacetylated, e.g. by heating with aqueous methylamine under reflux preferably in an inert atmosphere, e.g. $N_2$, and then cooled to yield a solution containing the compound of formula I which is optionally treated with charcoal and filtered. Concentration of the filtrate gives a solid which is recrystallized from $H_2O$ to give a crystalline product.

The compound of formula II may be obtained in similar fashion by reacting the compound of formula IV wherein R is Ac with acetic anhydride in the presence of a catalyst, e.g. $ZnCl_2$, to give acetoxymethyl 1,3-diacetoxy-2-propyl ether of the formula

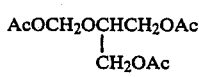   VI

This reaction takes place under similar conditions as used to form compound V from compound III wherein R is Ac.

The compound of formula VI is then purified and reacted with diacetylguanine of formula VII, under conditions similar to those used to react the compound of formula V with diacetylguanine, to form 2-acetamido-9-(1,3-diacetoxy-2-propoxymethyl)hypoxanthine of formula IX as a viscous oil which is crystallized by a procedure similar to that employed for the compound of formula VIII.

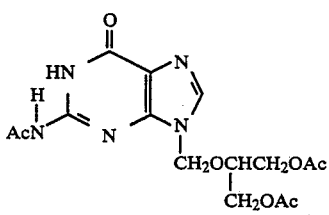   IX

The compound of formula IX is then converted to the crystalline product of formula II by treatment similar to that employed to convert the compound of formula VIII to formula I.

It is also possible if desired, to separate glycerol formal into its constituent compounds of formulas III and IV wherein R in each case is H and then to treat each separated compound as described above.

It is equally possible to form a mixture of compounds of formulas V and VI from glycerol formal by treating the latter directly with acetic anhydride in the presence of a catalyst, e.g., $ZnCl_2$. The resulting mixture may be chromatographed by HPLC. Fractions showing only the compound of formula V by analytical HPLC are concentrated under high vacuum and then reacted with diacetylguanine of formula VII as described above to give the compound of formula VIII which in turn is converted to the compound of formula I as described above.

Alternatively, the acetyl intermediates of formulas V and VI, each separately or as a mixture, can be converted to the more reactive halogen derivatives by treatment with hydrogen halide in a nonpolar solvent (hydrogen chloride in dichloromethane is preferred) wherein the terminal $AcOCH_2O—$ functionality is transformed to $XCH_2O—$ where X is a halogen (chlorine, bromine, or iodine). These halogen compounds can be used in alkylation reactions with protected guanines [per trimethylsilyl)guanine or diacetylguanine are two preferred derivatives] in nonpolar or dipolar solvents such as benzene, toluene, acetonitrile or dimethylformamide with or without an acid-acceptor substance such as triethylamine or powdered calcium carbonate as has been described in the literature, for example, in U.S. Pat. No. 4,199,574.

Chromatographic fractions containing primarily the compound of formula VI are rechromatographed by HPLC and those fractions of satisfactory purity are combined, concentrated under high vacuum and then reacted with diacetylguanine of formula VII as described above to give the compound of formula IX which in turn is converted to the compound of formula II as described above.

While the foregoing process description has referred specifically to compounds wherein the acyl group is acetyl, it is to be understood that the acyl group may equally be a straight or branched chain alkanoyl group of up to about 20 carbon atoms, which may be saturated or mono- or polyunsaturated and optionally substituted by aryl, substituted aryl, heterocyclyl, aralkyl, alkoxyalkyl or aryloxyalkyl group.

The acyl derivatives are preferably prepared by reacting the compounds of formula I or II with the appropriate acyl halide, acid anhydride, or other activated acyl species in the presence of an appropriate cosolvent such as, for example, pyridinedimethylformamide. In reactions with acyl halide or acid anhydrides the reaction rate and yield can be increased by addition of a tertiary amine such as triethylamine. 4-Dimethylaminopyridine is an effective catalyst. Other activated acyl species may be prepared by reaction of the acid with a suitable activating agent such as, for example, 1,1'-carbonyldiimidazole, N,N'-dicyclohexylcarbodiimide or by acylation of N-hydroxysuccinimide or 1-hydroxybenzotriazole by known methods. If the acyl group contains an amino, a hydroxyl, or a carboxyl group, this group must be protected during the acylation reaction. The preferred protection for the amino group is benzyloxycarbonyl and for the hydroxyl or carboxyl group is benzyl. Protecting groups are conveniently removed after the acylation by hydrogenolysis.

Compared to acycloguanosine, 9-(2-hydroxyethoxymethyl)guanine, the compounds of the present invention are more soluble and are more readily phosphorylated by viral enzymes, and have substantially greater activity in vivo than acycloguanosine. The compounds of the present invention may be employed as anti-viral compounds in mammalian or avian species either individually or in combination in dosage levels effective to impart an anti-herpes virus activity. Typically such levels are from about 0.01 to about 200 mg/kg/day. The compounds of the present invention may be formulated according to accepted pharmaceutical practice for administration orally, topically or by injection. Suitable oral dosage forms are tablets, capsules, elixirs or powders, while solutions or suspensions in, for example, phosphate buffered saline or water are suitable for injection. Examples of suitable topical formulations are gels, ointments, solutions or suspensions.

The acyl derivatives ($C_{1-20}$) of the compounds of the present invention have antimycoplasmal activity and are useful in treating or preventing this disease in swine and poultry.

The following Examples illustrate the present invention without, however, limiting the same thereto. All temperatures are expressed in degrees Celsius.

EXAMPLE 1

9-(2,3-Dihydroxy-1-propoxymethyl)guanine

A. Acetoxymethyl 2,3-Diacetoxy-1-propyl Ether

To a stirred mixture of 17.1 ml (20.8 g, 200 mmole) of glycerol formal containing a mixture of the compounds of formulas III and IV, there was added 60 ml of acetic anhydride, 6.7 ml of glacial acetic acid, and 2.0 g of anhydrous $ZnCl_2$. The mixture was stirred at ambient temperature under an $N_2$ atmosphere. The $ZnCl_2$ soon dissolved, and within a few minutes there was a strong exothermic reaction with the color of the solution turning light amber. After one hour, by which time the exothermic reaction had subsided, thin layer chromatography (TLC) (1:1 and 2:1 hexane-ethyl acetate) showed an apparently complete and clean reaction. After 4.5 hours, the solution was concentrated under high vacuum. The residual oil was taken up in 700 ml of diethyl ether and washed with 2×100 ml of a saturated $NaHCO_3$ solution, and then with 100 ml of $H_2O$. The ether solution was dried over $MgSO_4$, decolorized with charcoal, and filtered. The filtrate was concentrated under high vacuum to give 45.8 g (92%) of colorless residual oil. Analytical HPLC (7:3 hexane-ethyl acetate) showed only the two product isomers of formula V and VI. The bulk of the two product isomers (44.5 g) was subjected to HPLC in four batches of from 11 to 11.5 g each. All runs were performed under identical conditions using silica gel (two Waters Prep-500 packs), 7:3 hexane-ethyl acetate (250 ml per minute flow rate) with recycling (three cycles) and refractive index detection. Fractions were cut in the same place for each run, and fractions from the various runs were combined as they were collected. No clear separation of peaks was observed on the refractive index trace.

Fractions identified by analytical HPLC as pure compound of formula V (shorter retention time) were combined and concentrated under high vacuum to give 17.0 g of a colorless residual oil whose NMR ($CDCl_3$) was consistent for acetoxymethyl 2,3-diacetoxy-1-propyl ether.

B. 2-Acetamido-9-(2,3-diacetoxy-1-propoxymethyl)-hypoxanthine

A mixture of 2.61 g (11.1 mmole) of diacetylguanine (VII), 5.50 g (22.2 mmole) of acetoxymethyl 2,3-diacetoxy-1-propyl ether from Step A above and 55 mg of ethanesulfonic acid was heated in a flask fitted with a distillation adapter under low vacuum in an oil bath at 155°-160°. The mixture gradually thinned enough to permit magnetic stirring, and some distillate was collected. The mixture became homogenous after about 45 minutes and was cooled after 75 minutes. The viscous oil as taken up in about 100 ml of ethyl acetate and induced to crystallize with a yield of 1.23 g (29%) of nearly white crystals, mp 162.5°-165°. Thin layer chromatography (TLC) (9:1 $CHCl_3$—$CH_3OH$) showed a single spot.

C. 9-(2,3-Dihydroxy-1-propoxymethyl)guanine

A solution of 1.14 g (3.0 mmole) of 2-acetamide-9-(2,3-diacetoxy-1-propoxymethyl)hypoxanthine (VIII) from Step B above was heated at reflux in 40% aqueous methylamine with stirring under $N_2$ for 1 hour and then cooled. TLC (80:20:2 $CHCl_3$—$CH_3OH$—$H_2O$) showed complete conversion to the title compound (I). The light orange solution was treated with some charcoal and filtered through Super-Cel. Concentration of the filtrate gave a solid which was recrystallized from $H_2O$ (adjusted to about pH 6 with a few drops of $CH_3COOH$) to yield 687 mg of cream-colored crystals, mp 246°-247° dec.

EXAMPLE 2

9-(1,3-Dihydroxy-2-propoxymethyl)guanine

A. Acetoxymethyl 1,3-Diacetoxy-2-propyl Ether

After drying under high vacuum, fractions from step A of Example 1 which were high in content of formula VI (longer retention time) were combined to give 9.71 g of residual oil which was subjected to HPLC under the same conditions as described above. Fractions containing the compound of formula VI in satisfactory purity as determined by analytical HPLC were combined and concentrated under high vacuum to give 5.01 g of an almost colorless residual oil. Analytical HPLC indicated a ratio of compound of formula VI to the compound of formula V of approximately 15:1 based on peak heights. The NMR ($CDCl_3$) was consistent with this isomer ratio and was in accord with the identification of this compound as acetoxymethyl 1,3-diacetoxy-2-propyl ether.

B. 2-Acetamido-9-(1,3-diacetoxy-2-propoxymethyl)-hypoxanthine

A mixture of 3.76 g (16 mmole) of diacetylguanine (VII), 4.96 g (20 mmole) of acetoxymethyl 1,3-diacetoxy-2-propyl ether (VI), 40 mg of ethanesulfonic acid, and 15 ml of triglyme in a flask fitted with a distillation adapter was heated under low vacuum in an oil bath at 155°-160°. The mixture gradually thinned enough to stir, and a clear distillate was slowly collected. The reaction mixture became a clear solution after about 75 minutes. After 3 hours the solution was cooled, and the product was induced to crystallize. After standing, the thick mixture was diluted with a small volume of 1,2-dimethoxyethane. The solid was collected on a filter and washed with small volumes of 1,2-dimethoxyethane followed by ethyl acetate to give 3.27 g of cream-colored crystals consisting of a mixture of 9- and 7-alkylated isomers as determined by TLC (9:1 $CHCl_3$—MeOH). (The 9-isomer runs more slowly than the 7-isomer in this system). The mother liquor provided an additional 0.65 g of material. The combined crops (3.92 g) were chromatographed twice on a silica gel column (elution with 97:3 and then 96:4 $CH_2Cl_2$—MeOH). Fractions containing nearly pure 9-alkylated isomer were combined and concentrated. Crystallization of the residues from a minimum amount of 1,2-dimethoxyethane yielded a first crop of 665 mg (white crystals, mp 171.5°-172.5°) and a second crop of 189 mg (mp 173°-173.5°). Both crops consisted of the pure 9-alkylated product as determined by TLC in comparison with an earlier batch fully characterized by NMR and elemental analysis.

C. 9-(1,3-Dihydroxy-2-propoxymethyl)guanine

A solution of 838 mg (2.2 mmole) of 2-acetamido-9-(1,3-diacetoxy-2-propoxymethyl)hypoxanthine in 8.5 ml of 40% methylamine (aqueous) was stirred at gentle reflux under $N_2$ for 1 hour. The solution was then cooled and concentrated to dryness. The residual white solid was recrystallized from a minimum volume of $H_2O$ containing 2 drops of acetic acid. After standing in the refrigerator, the product was collected on a filter and washed with a small amount of $H_2O$, then acetone. The material was dried under high vacuum at 75° for 3 hours to giive 529 mg (90% based on hydration with 0.75$H_2O$) of white crystals, mp 249°-250° dec. The material was homogeneous by TLC (80:20:2 $CHCl_3$—MeOH—$H_2O$), and the structure was confirmed by NMR.

EXAMPLE 3

Acetoxymethyl 1,3-Diacetoxy-2-propyl Ether

A. 1,3-Dioxan-5-yl Acetate and 1,3-Dioxolane-4-methyl Acetate

A mixture of 10.0 g (96 mmole) of glycerol formal, 8.35 g (105 mmole) of pyridine, and 20 ml of acetic anhydride was stirred at ambient temperature under protection from moisture. After a period ranging from a few hours to 5 days, the solution was fractionally distilled under vacuum. The early fractions consisted primarily of pyridine, acetic acid, and acetic anhydride. The bulk of the product distilled at 56°–57° (1.1 mm). The product fractions (10.8 g) were separated into the 5- and 6-membered ring isomers by preparative HPLC on silica gel in 3:1 hexane-ethyl acetate with recycling. Fractions were identified and checked for purity by analytical HPLC. In total 3.19 g (23%) of 1,3-dioxolane-4-methyl acetate (shorter retention time) and 5.23 g (37%) of 1,3-dioxan-5-yl acetate (longer retention time) were obtained. The structures were confirmed by NMR.

B. Acetoxymethyl 1,3-Diacetoxy-2-propyl Ether

A solution of 6.0 g (41 mmole) of 1,3-dioxolane-4-methyl acetate and 0.4 g of zinc chloride in a mixture of 12 ml of acetic anhydride and 1.4 ml of glacial acetic acid was stirred at ambient temperature under $N_2$. An exotherm occurred, and after 1 hour TLC (2:1 hexane-ethyl acetate) indicated complete reaction. The solution was concentrated under high vacuum. The resulting liquid was dissolved in ether and washed thoroughly with saturated $NaHCO_3$ solution, then with $H_2O$. The ether layer was dried over $MgSO_4$, filtered, and concentrated to give 8.68 g of residual oil consisting of a mixture of the compound of formula VI (major) and the compound of formula V (minor). This material was combined with 3.50 g from a similar batch. The total of 12.18 g of crude product was purified by preparative HPLC on silica gel in 7:3 hexane-ethyl acetate with recycling. The fractions were checked for purity by analytical HPLC. Fractions of satifactory purity were combined and concentrated to give 5.84 g of the compound of structure VI ($\geq$90% pure). The structure and purity were confirmed by NMR.

EXAMPLE 4

Bromomethyl 1,3-Diacetoxy-2-propyl Ether

Acetoxymethyl 3-diacetoxy-2-propyl ether (250 mg, 1 mmole) was dissolved in dichloromethane presaturated with hydrogen bromide gas at 0°. The mixture was protected from moisture and stirred at 0° for 2 hours, then allowed to warm to ambient temperature with loss of excess hydrogen bromide. After three hours the solvents were removed under aspirator vacuum. The evaporation residue was treated successively with two 10 ml aliquots of dichloromethane, which were evaporated under aspirator vacuum. Finally the residual oil was dried under high vacuum until the sharp odor of hydrogen bromide was no longer evident. The resulting material may be used immediately in alkylation reactions. Protein magnetic resonance spectra of $CDCl_3$ solutions showed an appropriate downfield shift reflecting the change from $AcOCH_2O$ to $BrCH_2O$.

EXAMPLE 5

Chloromethyl 1,3-Diacetoxy-2-propyl Ether

A solution of 4.34 g (17.5 mmole) of acetoxymethyl 1,3-diacetoxy-2-propyl ether in 45 ml of methylene chloride was stirred at room temperature as a gentle stream of HCl was passed through it. After 2 hours the HCl stream was removed. The flask was stoppered and allowed to stir overnight at room temperature. Then the flask was placed in a water bath at 25°–30°, and the solution was purged with a stream of $N_2$ to remove most of the excess HCl. The remaining solution was concentrated by rotary evaporation. In order to remove traces of HCl, the residual oil was taken up in toluene and concentrated under high vacuum at room temperature. This process was repeated three more times. After vacuum drying at room temperature, the yield of colorless residual oil was 3.83 g (97%). The NMR spectrum indicated complete conversion to product.

EXAMPLE 6

2-Acetamido-9-(1,3-diacetoxy-2-propoxymethyl)-hypoxanthine

A mixture of 2.57 g (18 mmole) of guanine, 1.8 g of ammonium sulfate, and 126 ml of hexamethyldisilazane was stirred at reflux under $N_2$. The solid gradually dissolved. After 2 days the solution was cooled and concentrated under high vacuum. The viscous, residual oil was dissolved in about 28 ml of dry toluene and maintained under $N_2$ as a solution of 5 g (22.3 mmole) of chloromethyl 1,3-diacetoxy-2-propyl ether in 12 mol of dry toluene was added. The resulting solution was heated at reflux under $N_2$ for 1.5 hours. It was then cooled, concentrated, and dried under high vacuum. The viscous, orange residual oil was treated with 30 ml of water and 30 ml of saturated sodium bicarbonate solution. The mixture was swirled with warming on a steam bath for 5 minutes, during which time the residue solidified. After cooling, the solid was collected on a filter and washed with a small volume of water. Although this cream-colored solid (4.6 g) gave a single spot on TLC (80:20:2 $CHCl_3$—MeOH—$H_2O$), NMR showed that it contained 10–15% of the 7-alkylated isomer in addition to the desired 9-isomer. The material was combined with 0.6 g of similar material from other runs and was suspended in 184 ml of acetic anhydride. The mixture was heated at 97° for 18 hours by which time nearly all of the solid had dissolved, and TLC showed complete acetylation. The reaction was cooled and concentrated under vacuum. Treatment of the residue with 200 ml of methylene chloride gave a solid, which was isolated by filtration and washed once with methylene chloride. Recrystallization from methylene chloride gave 0.55 g of pure 9-isomer. The filtrates were passed through a column containing 40 g of silica gel. Elution with 97:3 $CH_2CL_2$—MeOH gave 4.5 g of partially purified product. Upon recrystallization from methylene chloride (about 45 ml), 3.0 g of pure 9-isomer was obtained.

EXAMPLE 7

9-(1,3-Diacetoxy-2-propoxymethyl)guanine

A mixture of 50.0 g (0.33 mole) of guanine, 33 g of ammonium sulfate, and 2.2 l of hexamethyldisilazane was stirred at reflux under $N_2$ for 3 days, during which time all of the solid dissolved. The solvent was then removed by distillation under reduced pressure. To the very viscous, orange residual oil was added under $N_2$ 84 g (0.34 mole) of acetoxymethyl 1,3-diacetoxy-2-propyl ether, which formed in second liquid phase at the bottom of the flask. The flask was fitted with a distillation adapter, and the mixture was heated under low vacuum in an oil bath at approximately 135°. After an induction period lasting several minutes, boiling began and soon became quite vigorous. Distillation of trimethylsilyl acetate (along with any residual hexamethyldisilazane) proceeded rapidly at first but slowed after 30 minutes. After 2 hours the mixture was added to 1.3 l of 90% EtOH. The mixture was heated to boiling and maintained there until the separated gummy material was transformed to a tractable solid. The solid (8.2 g, consisting almost exclusively of guanine) was removed by filtration while hot. The filtrate was allowed to stand overnight, resulting in separation of an orange-brown gum. The supernatant was decanted away from the gum, filtered, and then concentrated to small volume. The solid which separated on concentration was collected on a filter and washed with $H_2O$, then with some EtOH, to give 15.4 g of cream-colored crystals. By NMR, this material was solely the -alkylated isomer, although TLC indicated partial side chain deactylation. The material was suitable for deprotection without further purification.

Further processing of the mother liquor, and of the gum which had been removed by decantation, gave additional crops consisting of varying ratios of 9- and 7-alkylated isomers (partially deacetylated). These less pure crops were preferably converted to fully acetylated derivatives (O,O',N²-triacetyl) prior to chromatographic purification (silica gel, elution with $CH_2Cl_2$—MeOH). Typical acetylation conditions consisted of stirring a mixture of 10 g of the crude guanine derivative and 400 ml of acetic anhydride at 95°–100° overnight, followed by concentration and chromatography.

EXAMPLE 8

9-(1,3-Diacetoxy-2-propoxymethyl)guanine

A mixture of 205 mg (0.75 mmole) of 9-(1,3-dihydroxy-2-propoxymethyl)guanine monohydrate, 1.5 ml of acetic anhydride, 6 ml of dry dimethylformamide, and 1.5 ml of dry pyridine was stirred at room temperature under a drying tube for 4 days. Then the mixture was diluted with 15 ml of $Et_2O$. The solid was collected on a filter and washed with $Et_2O$. After recrystallization from 2-methoxyethanol, yield of colorless crystals=149 mg (59%), m.p. 239°–240°. The material was homogenous by TLC (9:1 $CHCl_3$—MeOH), and NMR confirmed the assigned structure.

Anal. ($C_{13}H_{17}N_5O_6$). Calcd.: C, 46.01; H, 5.05; N, 20.64. Found: C, 45.71; H, 5.04; N, 20.36.

EXAMPLE 9

9-(1,3-Dipropionyloxy-2-propoxymethyl)guanine

A mixture of 205 mg (0.75 mmole) of 9-(1,3-dihydroxy-2-propoxymethyl)guanine monohydrate, 1.5 ml of propionic anhydride, 6 ml of dry dimethylformamide, and 1.5 ml of dry pyridine was stirred at room temperature under a drying tube. After 4 days the mixture was diluted with 25 ml of ether. The solid was collected on a filter and washed with ether. Recrystallization from isopropanol gave 136 mg (50%) of white crystals, m.p. 196°–197.5°. The material ran as a single spot on TLC (9:1 $CHCl_3$—MeOH), and the structure was confirmed by NMR.

Anal. ($C_{15}H_{21}N_5O_6$). Calcd.: C, 49.04; H, 5.76; N, 19.07. Found: C, 48.96; H, 5.83; N, 19.26.

EXAMPLE 10

9-(1-Hydroxy-3-octanoyloxy-2-propoxymethyl)guanine

A suspension of 410 mg (1.5 mmole) of 9-(1,3-dihydroxy-2-propoxymethyl)guanine monohydrate in 6 ml of dry dimethylformamide and 1.5 ml of dry pyridine was stirred under a drying tube with cooling in an ice bath as a solution of 489 mg (3.0 mmole) of octanoyl chloride in 1.5 ml of dimethylformamide was added dropwise by syringe over approximately 5 minutes. The mixture was allowed to warm gradually to room temperature, and after 24 hours it was concentrated under high vacuum. The residual oil was purified by preparative TLC on nine 1000-$\mu$ silica gel plates (developed in 5:1 $CHCl_3$—MeOH). The product bands were isolated, combined, and extracted with dimethylformamide. Concentration of the extracts under high vacuum gave a gummy residue. Crystallization from isopropanol gave a material which again turned gummy on the filter. However, thorough trituration with ether yielded 105 mg (18%) of very pale yellow crystals, m.p. 201.5°–203.5°.

EXAMPLE 11

9-(1,3-Dioctanoyloxy-2-propoxymethyl)guanine

A mixture of 2.73 g (10 mmole) of hydrated 9-(1,3-dihydroxy-2-propoxymethyl)guanine, 40 ml of dry dimethylformamide, and 14 ml of pyridine was stirred under nitrogen with cooling in an ice bath as a solution of 6.80 ml (6.51 g, 40 mmole) of octanoyl chloride in 14 ml of dimethylformamide was added dropwise. After stirring overnight at room temperature, the mixture was concentrated under vacuum. The residual oil was partitioned between ethyl acetate and water. The ethyl acetate layer (containing some suspended solid) was evaporated to dryness. Chromatography of the residue on a column of silica gel (gradient elution with methylene chloride containing 3 to 7% methanol) yielded 2.38 g (47%) of white crystals, m.p. 161° to 162° C. The NMR spectrum and mass spectrum were consistent with the assigned structure. The material was homogeneous by TLC in 12:1 $CHCl_3$—MeOH.

Anal. Calcd. for $C_{25}H_{41}N_5O_6$: C, 59.15; H, 8.14; N, 13.80. Found: C, 59.15; H, 8.09; N, 13.60.

This compound gave a 75% inhibition of mycoplasmal growth in chickens when administered systemically at a dosage level of 875 $\mu$g/bird.

EXAMPLE 12

Sodium 9-(1,3-Dihydroxy-2-propoxymethyl)guanine cyclic monophosphate

A suspension of 5.91 g (23.2 mmoles) of anhydrous 9-(1,3-dihydroxy-2-propoxymethyl)guanine in a solution of 3.6 g (2.2 ml; 23.6 mmoles) of phosphorous oxychloride in 60 ml of anhydrous triethyl phosphate was stirred at room temperature for five hours. The largely clarified mixture was filtered, and the filtrate was poured into 600 ml of stirred hexane. After about five minutes the supernatent hexane was decanted from the precipitated product, and the residue was heated with a second 600 ml portion of hexane. After the supernatant hexane was decanted and the residue was dried in vacuo, 15.9 g of a solid product was obtained. The solid was largely dissolved in 800 ml of deionized water and the cloudy mixture was titrated to pH 7 with 5N potassium hydroxide and then 1N potassium hydroxide. The neutralized mixture was filtered and the filtrate was lyophilized yielding 9.25 g of product.

A specimen of the lyophilization residue was analyzed by high performance liquid chromatography using a Whatman Partisil ™ PXS 10/25 SAX ion exchange column with 0.05M pH 6.6 phosphate buffer elution and ultraviolet absorption detection at 252 nm. the product exhibited three peaks with retention times of about 4 minutes, 7 minutes and 9 minutes. After authentic specimens of sodium and potassium 9-(1,3-dihydroxy-2-propoxymethyl)guanine cyclic and acylic monophosphate were isolated as disclosed in this and other examples in this patent application and subjected to high performance liquid chromatography in the above system, the cyclic monophosphate was associated with a retention time of about 4 minutes and the acyclic phosphate with a retention time of about 7 minutes.

The lyophilized mixture of potassium salts was dissolved in 1 liter of deionized water and filtered through a fluted filter paper. The filtrate was slowly passed through a 4–5 cm diameter column of 460 ml (644 milliequivalents) of 200–400 mesh Bio Rad AGL-X8 anion exchange resin on the bicarbonate cycle. Next, a gradient of 0.05M–0.5M potassium bicarbonate from a gradient elution chamber containing 2 liters of 0.05M and 0.5M potassium bicarbonate was pumped through the column and fractions of about 20 ml were collected at 8-minute intervals. At fraction 191, the eluent was changed to 0.05M potassium bicarbonate and samples of 20–25 ml were collected at 6.8-minute intervals. The elution pattern was monitored by ultraviolet absorption at 252 nm and certain component fractions of the various elution peaks were further characterized by high performance liquid chromatography in the Whatman Partisil ™ PXS 10/25 SAX ion exchange column using 0.05M pH 6.6 phosphate elution. On the basis of these data certain fractions were combined and worked up as follows:

Fractions 450–540 (1680 ml) characterized by a single peak with a retention time of about 5 minutes in the above high performance liquid chromatography system, were combined and treated with 600 ml (1020 milliequivalents) of 200–400 mesh Bio Rad AG50W-X8 cation exchange resin on the acid cycle. The stirred mixture was kept under a modest vacuum to remove carbon dioxide before it was filtered. The mixture was filtered and the resin was washed with small portions of deionized water. The combined filtrates were concentrated to a 150 ml volume in vacuo at about 35° and the precipitated product, in the form of the free acid, was isolated by filtration and dried in vacuo to yield 445 mg of 9-(1,3-dihydroxy-2-propoxymethyl)guanine cyclic monophosphate. The product was crystalline according to microscopy in polarized light, showed an ultraviolet absorption maximum at 252 nm ($\epsilon$ 10600, in 0.1M pH 7 phosphate), and gave a nuclear magnetic resonance spectrum fully in accord with the projected structure. Concentration of the mother liquors yielded an additional 46 mg of the free acid form of the product. Titration of the mother liquors to pH 7 followed by lyophilization yielded 196 mg of sodium 9-(1,3-dihydroxy-2-propoxymethyl)guanine cyclic monophosphate. The latter compound, may at times be contaminated with small amounts of water soluble inorganic salts and may be purified by exclusion chromatography or by ion exchange chromatography on Bio Rad AG1-X8 anion exchange resin on the formate cycle.

The pure sodium salt was also obtained by titration of the crystalline free acid as follows:

A suspension of 213 mg of crystalline 9-(1,3-dihydroxy-2-propoxymethyl)guanine cyclic monophosphate was titrated to pH 7 with 1N sodium hydroxide and the solution was lyophilized yielding 227 mg of sodium 9-(1,3-dihydroxy-2-propoxy-methyl)guanine cyclic monophosphates. A dried sample of this product had an ultraviolet absorption maximum at 252 nm ($\epsilon$ 11800 in 0.1M pH 7 phosphate).

The 200 MHz NMR spectrum of the cyclic product in $D_2O$ is characterized by signals from two equivalent methylenes that have shifted downfield on monophosphorylation. The spectrum is characterized by the following chemical shifts.

| | | | | |
|---|---|---|---|---|
| $\delta 3.94$ | $\begin{array}{c} \diagup C \\ O-C \\ \mid \diagdown \\ H \quad C \end{array}$ | m | 1H | |
| $\delta 4.25$ | $P-O-CH$ eq | d, d, d | 2H | (JH, H gem 12.5 Hz)<br>(JP—OCH eq 19.5 Hz)<br>(JH, H vic eq 2.2 Hz) |
| $\delta 4.39$ | $P-O-CH_{ax}$ | d, d, d | 2H | (JH, H gem 12.5 Hz)<br>(JP—OCH ax 5.0 Hz)<br>(JH, H vic ax 1.8 Hz) |
| $\delta 5.64$ | $N-CH_2O$ | s | 2H | |
| $\delta 7.99$ | $C_8-H$ | s | 1H | |

Additional confirmation of structure is obtained when the predicted pattern of shifts is realized for the $P-O-CH_2$ groups on irradiation of the

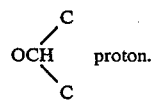 proton.

In a Varian AX-10 high performance liquid chromatography anion exchange column using a gradient of 10–1000 mM unbuffered $KH_2PO_4$, the cyclic product has a retention time of 4.3 minutes whereas the enzymically derived acyclic monophosphate has a retention time of 4.8 minutes. The synthetic cyclic monophosphate is clearly separated from the acyclic enzymically-derived monophosphate when a mixture of the two is subjected to HPLC in the above system.

As an alternative, the sodium or potassium salt of the cyclic monophosphate may be isolated from the Bio Rad AG1-X8 bicarbonate eluate fractions without isolation of the crystalline free acid. A combination of fractions amounting to about 800 ml of 0.5M $KHCO_3$ was treated with 325 ml (552 mmoles) of 200–400 mesh AG50W-X8 cation exchange resin on the acid cycle. The stirred mixture was kept under modest vacuum for fifteen minutes to remove carbon dioxide and was filtered. The filtrate was concentrated to about a 100 ml volume which was then titrated to pH 7 with 1N sodium hydroxide. Lyophilization of the resulting solution yielded 529 mg of the sodium salt of the cyclic phosphate that was contaminated with a small amount of water soluble inorganic salts.

To desalt the product, 200 mg of the sodium salt was dissolved in 1.5 ml of deionized water and put on a 1.5 cm diameter column of 6 ml of Bio Rad 200–400 mesh AG1-X8 anion exchange resin on the formate cycle. After about 35 ml of deionized water was passed through the column, elution was begun with 2N ammonium formate solution. Fractions of 3.5 ml volume were collected at 3 minute intervals and the ultraviolet absorption at 250 nm of each fraction was measured and plotted versus tube number. On the basis of the shape of the curve obtained in the above plot, fractions 13–28 were combined and put on a 2–3 cm diameter column of 120 ml (204 milliequivalents) of 200–400 mesh Bio Rad AG50W-X8 cation exchange resin. The column was eluted with water and 13.5 ml fractions were collected at 4.5-minute intervals. The elution pattern was monitored by ultraviolet absorption at 252 nm and on the basis of the plot, fractions 22–40 were combined and concentrated to dryness. The residue was taken up in 10 ml of deionized water and titrated to pH 7 with 0.1N NaOH. Lyophilization of the neutralized solution yielded 106 mg of sodium 9-(1,3-dihydroxy-2-propoxymethyl)guanine cyclic monophosphate.

EXAMPLE 13

Disodium 9-(1,3-dihydroxy-2-propoxymethyl)-guanine acyclic monophosphate

Preparation 1

In the phosphorylation of 9-(1,3-dihydroxy-2-propoxymethyl)guanine with phosphorus oxychloride to yield the corresponding cyclic monophosphate, the crude condensation product was purified by ion exchange chromatography on Bio Rad AG1-X8 ($CO_3^=$). In the course of elution with 0.5M potassium bicarbonate as described in the example for preparation of the cyclic monophosphate, a discrete peak consisting of fractions 245–248 was separated and found to contain the corresponding acyclic compound dipotassium 9-(1,3-dihydroxy-2-propoxymethyl)guanine acyclic monophosphate. Using a Partisil ™ PXS 10/25 SAX high performance liquid chromatography column and elution with 0.05M pH 6.6 phosphate buffer, this peak contained material with retention times of about 5 and 8 minutes. The authentic acyclic monophosphate is associated with a retention time of 7–8 minutes in the same system. Analysis of this combination of fractions on a Varian AX-10 high performance liquid chromatography anion exchange column using gradient elution with 10–400 mM unbuffered $KH_2PO_4$ showed that about 40% of the material was dipotassium 9-(1,3-dihydroxy-2-propoxymethyl)guanine acyclic monophosphate.

Preparation 2

A solution of 44.5 mg of sodium 9-(1,3-dihydroxy-2-propoxymethyl)guanine cyclic monophosphate in 4 ml of 5N sodium hydroxide was heated at 55°–60° C. under a nitrogen blanket for eight hours. The reaction mixture was diluted to a 12 ml volume with deionized water and passed slowly through a 30 ml (2 cm diameter×12 cm length) column of Bio Rad AG50W-X8 cation exchange resin on the sulfonic acid cycle. The column was eluted with deionized water and 5 ml fractions were collected at 4-minute intervals. After fraction 60 was collected, 12 ml fractions were collected every 4 minutes. The various fractions were evaluated by ultraviolet absorption at 252 nm and also by high performance liquid chromatography on a Partisil ™ PXS 10/25 SAX anion exchange column using 0.05M pH 6.6 phosphate buffer elution. Fractions 45–64, which consisted exclusively of material with a retention time of about 7.5 minutes were combined, titrated to pH 7 with 0.1N sodium hydroxide and then lyophilized to yield 30 mg of disodium 9-(1,3-dihydroxy-2-propoxymethyl)-guanine acyclic monophosphate. A 200 MHz nuclear magnetic spectrum of the product in deuterium oxide is fully in accord with the acyclic monophosphate structure.

Anal. Calcd. for $C_9H_{12}N_5O_7PNa_2$ (279.19): N, 18.47; C, 28.51; H, 3.19; P, 8.17; Na, 12.13. Found: N, 18.07; C, 28.67; H, 3.36; P, 8.51, Na, 11.90 (by atomic absorption). $\lambda$max 252 nm, $\epsilon$ 9600 (0.1M pH 7 phosphate).

EXAMPLE 14

9-[1,3-Bis(phenoxyacetoxy)-2-propoxymethyl]guanine

A suspension of 273 mg (1.0 mmole) of 9-(1,3-dihydroxy-2-propoxymethyl)guanine monohydrate in 4 ml of dry dimethylformamide and 1.4 ml of dry pyridine was stirred under nitrogen with cooling in an ice bath as a solution of 552 $\mu$l (682 mg, 4 mmole) of phenoxyacetyl chloride in 1.6 ml of dimetylformamide was added dropwise by syringe through a septum over a period of 10 minutes. After the ice had melted, the mixture was allowed to warm gradually to room temperature. A pale yellow solution was obtained. After 15 hours the solution was concentrated under high vacuum with mild warming. The golden residual oil was chromatographed on a silica gel column (gradient elution from 98:2 $CH_2Cl_2$—MeOH to 92:8$CH_2Cl_2$—MeOH). Fractions containing nearly pure product were combined and concentrated to give an oil which solidified on trituration with ether-acetone. Recrystallization from a small volume of acetonitrile gave 114 mg of white crystals, m.p. 114°–116°. Structure and purity were confirmed by NMR and TLC (9:1CHCl$_3$—MeOH). A second crop of 66 mg was obtained from the mother liquor.

Anal. ($C_{25}H_{25}N_5O_8$). Calcd.: for 93.5% $C_{25}H_{25}N_5O_8.H_2O+6.5\%$ inorganic silica gel: C, 51.84; H, 4.70, N, 12.09. Found: C, 51.94; H, 4.74; N, 11.99.

EXAMPLE 15

9-(2,3-Dibenzoyloxy-1-propoxymethyl)guanine

A suspension of hydrated 9-(2,3-dihydroxy-1-propoxymethyl)guanine (1 mmole) in 4 ml of dry dimethylformamide and 1.4 ml of dry pyridine was stirred under nitrogen in an ice bath as a solution of benzoyl chloride (4 mmole) in 1.6 ml of dimethylformamide was added dropwise. The mixture was allowed to warm gradually to room temperature. After stirring overnight, the solution was concentrated under high vacuum. The residue was chromatographed on silica gel (elution with $CH_2Cl_2$—MeOH) to give a glossy residue. Trituration with ether and then with chloroform gave an amorphous white solid which softened 70° C. Structure and purity were confirmed by NMR, TLC (9:1CHCl$_3$—MeOH), and mass spectrum.

Anal. Calcd for 90% ($C_{23}H_{21}N_5O_6 2H_2O$)+10% inorganic silica gel: C, 49.77; H, 4.54; N, 12.62. Found: C, 49.76; H, 4.58; N, 12.55.

EXAMPLE 16

9-(1,3-Diisovaleryloxy-2-propoxymethyl)guanine

A suspension of hydrated 9-(1,3-dihydroxy-2-propoxymethyl)guanine (1 mmole) in 4 ml of dry dimethylformamide and 1.4 ml of dry pyridine was stirred under nitrogen in an ice bath as a solution of isovaleryl chloride (4 mmole) in 1.6 ml of dimethylformamide was added dropwise. After warming gradually to room temperature, the mixture was stirred overnight. The resulting solution was evaporated under high vacuum with mild warming. The residue was partitioned between ethyl acetate and water, and the ethyl acetate phase was concentrated. Chromatography of the residue on silica gel (elution with $CH_2Cl_2$—MeOH) gave 192 mg (52%) of white solid, m.p. 215°–217° (raised to 216°–218° after recrystallization from isopropanol). Structure and purity were confirmed by NMR and TLC (9:1$CHCl_3$—MeOH).

Anal. Calc'd for $C_{17}H_{29}N_5O_4$: C, 53.89; H, 6.91; N, 16.53 Found: C, 54.22; H, 6.92; N, 16.42.

EXAMPLE 17

9-[1,3-Bis(phenylacetoxy)-2-propoxymethyl]guanine

A suspension of 273 mg (1 mmole) of hydrated 9-(1,3-dihydroxy-2-propoxymethyl)guanine in 4 ml of dry dimethylformamide and 1.4 ml of dry pyridine was stirred in an ice bath under nitrogen as a solution of 529 μl (618 mg, 4 mmole) of phenylacetyl chloride in 1.6 ml of dimethylformamide was added dropwise. The mixture was allowed to warm gradually to room temperature. After stirring overnight, the solution was concentrated in vacuo. Chromatography of the residual oil on silica gel (elution with $CH_2Cl_2$—MeOH) which solidified on scratching. This material was triturated with ether and vacuum dried to give an amorphous white solid, which softened >65° C. Structure and purity were verified by NMR and TLC (9:1$CHCl_3$—MeOH).

Anal. Calcd. for 95.8% ($C_{25}H_{25}N_5O_6.2H_2O$)+4.2% inorganic silica gel: C, 53.62; H, 5.22; N, 12.50. Found: C, 53.93; H, 5.13; N, 12.29.

EXAMPLE 18

9-[1,3-Bis(10-undecenoyloxy)-2-propoxymethyl]guanine

To a stirred ice-cooled suspension of 273 mg (1 mmole) of hydrated 9-(1,3-dihydroxy-2-propoxymethyl)guanine monohydrate in 4 ml of dry dimethylformamide and 1.4 ml of dry pyridine was added dropwise under protection from moisture a solution of 860 μl (812 mg, 4 mmole) of 10-undecenoyl chloride in 1.6 ml of dimethylformamide. After warming to room temperature and stirring overnight, the solution was concentrated in vacuo. The residue was extracted with ethyl acetate. Concentration of the filtered extracts gave an oil which was purified by silica gel column chromatography (gradient elution with 99:1 to 99:5$CH_2Cl_2$—MeOH). Fractions containing nearly pure product were combined and concentrated. The residue was taken up in ethyl acetate, treated with charcoal, and filtered. Most of the product remained bound to the filter cake but was extracted by washing with dimethylformamide. Evaporation gave a waxy residue which was taken up in methylene chloride and filtered. Concentration of the filtrate gave 251 mg of cream-colored, waxy semi-solid, whose structure was confirmed by 200 MHz NMR.

Anal. Calcd. for 97%$C_{31}H_{49}N_5O_6$+3% inorganic silica gel: C, 61.45; H, 8.15; N, 11.56. Found (average of 2 runs) C, 61.58; H, 8.30; N, 11.42.

EXAMPLE 19

9-[1,3-Bis(methoxyacetoxy)-2-propoxymethyl]guanine

Reaction of hydrated 9-(1,3-dihydroxy-2-propoxymethyl)guanine (1 mmole) with methoxyacetyl chloride (4 mmole) according to the method used for 9-[1,3-bis(phenoxyacetoxy)-2-propoxymethyl]guanine (Example 14) gives, after chromatography, the desired product. Confirmation of structure and purity are obtained by NMR and TLC (9:1$CHCl_3$—MeOH).

EXAMPLE 20

9-[1,3-Bis(imidazol-1-ylcarbonyloxy)-2-propoxymethyl]-guanine

A mixture of 55 mg (0.2 mmole) of 9-(1,3-dihydroxy-2-propoxymethyl)guanine monohydrate, 130 mg (0.8 mmole) of 1,1'-carbonyldiimidazole, and 2 ml of dry dimethylformamide was stirred under nitrogen at 95°–100° for 1.5 hours, during which time a clear solution was obtained followed by precipitation of product. After cooling, the precipitate was collected on a filter and washed with some dimethylformamide and then with acetone to give 37 mg of white crystals, m.p. 252°–253° dec. The NMR spectrum was in accord with the assigned structure.

Anal. ($C_{17}H_{17}N_9O_6$). Calcd.: C, 46.05; H, 3.87; N, 28.43; Found: C, 45.68; H, 3.90; H, 3.90; N, 28.18.

EXAMPLE 21

9-(2,3-Diacetoxy-1-propoxymethyl)guanine

A mixture of 5.34 g (20 mmole) of hydrate 9-(2,3-dihydroxy-1-propoxymethyl)guanine, 40 ml of acetic anhydride (increased to 100 ml after several days), 40 ml of pyridine (increased to 80 ml after a few days) and 160 ml of dimethylformamide was stirred at room temperature under a drying tube for a total of 20 days and then concentrated in vacuo. The residue was triturated with 30 ml of methylene chloride and diluted with 100 ml of ether. The solid was collected on a filter, washed with ether, and recrystallized from dioxane-acetic acid to give (after washing with acetone and drying) 4.18 g (62%) of slightly off-white powder, mp 222.5° to 224° C. Structure and purity were confirmed by NMR and TLC (9:1$CHCl_3$—MeOH).

Anal. Calcd for $C_{13}H_{17}N_5O_6$: C, 46.01; H, 5.05; N, 20.64. Found: C, 45.64; H, 4.97; N, 20.37.

EXAMPLE 22

9-(2,3-Dioctanoyloxy-1-propoxymethyl)guanine

A suspension of 267 mg (1 mmole) of hydrated 9-(2,3-dihydroxy-1-propoxymethyl)guanine in 4 ml of dry dimethylformamide and 1.4 ml of dry pyridine was stirred under nitrogen at 0° C. as 0.68 ml (650 mg, 4 mmole) of octanoyl chloride in 1.6 ml of dimethylformamide was added dropwise. The mixture was allowed to warm gradually to room temperature. After stirring overnight, it was concentrated in vacuo. The residue was chromatographed on a silica gel column (gradient elution with methylene chloride containing 0–5% methanol) to give 197 mg (39%) of solid, which was triturated and washed with chloroform and ether. The white solid softened >145° C. and was shown to be of good purity by NMR and TLC (9:1$CHCl_2$—MeOH).

Anal. Calcd. for 94% ($C_{25}H_{41}N_5O_6.H_2O$+6% inorganic silica gel: C, 53.69; H, 7.75; N, 12.53. Found: C, 53.77; H, 7.59; N, 12.52.

EXAMPLE 23

9-[2,3-Bis(phenoxyacetoxy)-1-propoxymethyl]guanine

A suspension 267 mg (1 mmole) of hydrated 9-(2,3-dihydroxy-1-propoxymethyl)guanine in 4 ml of dry dimethylformamide and 1.4 ml of dry pyridine was stirred under nitrogen in an ice bath as a solution of 0.55 ml (682 mg, 4 mmole) of phenoxyacetyl chloride in 1.6 ml of dimethylformamide was added dropwise. After gradually warming to room temperature, the mixture was stirred overnight and then evaporated under vacuum. Chromatography of the residue on silica gel (elution with methylene chloride-methanol) gave a white solid, which was recrystallized from isopropanol, yielding 30 mg with m.p. 95°–100° C. The material was judged to have good purity by NMR and TLC (9:1CHCl$_3$—MeOH).

Anal. Calcd for 93.6% ($C_{25}H_{25}N_5O_8$.0.75-$H_2O$)+6.4% inorganic silica gel: C, 52.31; H, 4.65; N, 12.20. Found: C, 52.53; H, 4.66; N, 12.05.

EXAMPLE 24

9-(2,3-Diazidoacetoxy-1-propoxymethyl)guanine

A solution of 0.84 ml (8.4 mmol) of azidoacetyl chloride in 5 ml of dimethylformamide is added dropwise over a period of 10 minutes to an ice-cooled stirred suspension of 0.66 g (2.5 mmol) of 9-(2,3-dihydroxy-1-propoxymethyl)guanine and 0.35 ml (2.5 mmol) of triethylamine in dry dimethylformamide (40 ml). After stirring for 45 minutes at 0°, the reaction is allowed to warm to ambient temperature for 30 minutes and is quenched with 7% sodium bicarbonate solution (15 ml). The mixture is evaporated to dryness in vacuo and the residue is extracted with dichloromethane (3×50 ml). The organic extract is washed with cold water, dried, and evaporated to a residue which is recrystallized from an appropriate solvent such as aqueous methanol to furnish the pure product.

EXAMPLE 25

9-[2,3-Bis(N-carbobenzyloxyglycyloxy)-1-propoxymethyl]guanine

To a solution of 1.65 g of N-carbobenzyloxyglycine in 4 ml of dry dimethylformamide was added 1.48 g of N,N'-dicyclohexylcarbodiimide, and stirring was continued at room temperature for 1 hour, during which time N,N'-dicyclohexyurea precipitated. The reaction mixture was then filtered directly into another flask containing a suspension of 9-(2,3-dihydroxy-1-propoxymethyl)guanine in 4 ml of dry dimethylformamide (largely in solution after mild warming). The resulting mixture was treated with a few crystals of 4-dimethylaminopyridine and then stirred under nitrogen at room temperature for 21 hours. The mixture was filtered, and the filtrate was concentrated in vacuo. The gelatinous residue was seeded with crystals obtained by trituration with acetonitrile. Crystallization occurred on standing over the weekend. This material was isolated and dissolved in tetrahydrofuran-water (60:40) and evaporated onto silica gel. This was layered on top of a column of silica gel, which was then eluted with 80:20:2 chloroform-methanol-water. Fractions containing pure diacylated produt by TLC were combined to give a total of 145 mg of the title compound. The structure was confirmed by 200 MHz NMR.

EXAMPLE 26

9-(2,3-Diglycyloxy-1-propoxymethyl)guanine

Method 1:

The product from Example 24 (1.23 g) is hydrogenated (H$_2$ pressure=40 psi) in aqueous ethanol in the presence of 10% of Pd/C (1.0 g) and 1.0N HCl (4 ml). After the reaction is shown to be complete by TLC (about 1.5 hours), the catalyst is filtered and washed well with water. Volume reduction in vacuo causes the product to crystallize. Filtration and recrystallization from aqueous ethanol gives the title compound.

Method 2:

This material is prepared by hydrogenation of 9-[2,3-bis(N-carbobenzyloxyglycyloxy)-1-propoxymethyl]guanine as described for the sysnthesis of 9-(2,3-dialanyloxy-1-propoxymethyl)guanine (Example 27).

EXAMPLE 27

9-(2,3-Dialanyloxy-1-propoxymethyl)guanine

A mixture of 0.54 g (2 mmol) of 9-(2,3-dihydroxy-1-propoxymethyl)guanine, 1.026 g (4.3 mmol) of N-carbobenzyloxy-DL-alanine, 0.04 g anhydrous p-toluenesulfonic acid, and 1.755 g (5.6 mmol of N,N'-dicyclohexylcarbodiimide in dry pyridine (80 ml) is stirred for 24 hours. Acetic acid (1 ml) is added and the mixture is stirred for an additional hour. The reaction mixture is filtered and the residue is washed with methanol. The filtrate is evaported to dryness in vacuo and chromatographed on silica gel (CH$_2$Cl$_2$/MeOH, 9:1). Evaporation of the product-containing fractions and recrystallization from aqueous ethanol gives the protected ester. Removal of the CBZ group is accomplished by hydrogenation in 50% aqueous methanol (300 ml/1.0 g protected ester/containing one equivalent of HCl as a 0.5 N solution using 10% Pd/C (0.5 g/1.0 g protected ester) at 40 psi of hydrogen for 2 hours. The catalyst is filtered, washed with water and the filtrate is evaporated to dryness in vacuo. Recrystallization from aqueous ethanol furnishes the title compound.

EXAMPLE 28

9-[2,3-(Di-3-carboxypropyloxy)-1-propoxymethyl)guanine

A solution of 9-(2,3-dihydroxy-1-propoxymethyl)guanine (1.37 g, 5 mmol), 2.0 g of succinic anhydride, 1.4 ml of anhydrous triethylamine in dry dimethylformamide (75 ml) is heated in an oil bath at 60°. When the reaction is complete (24 hours) the mixture is cooled and evaporated to dryness in vacuo. The residue is resuspended in ice-water (50 ml) and the pH is adjusted to 2 with 2NHCl. The white precipitate is filtered, thoroughly washed with ice-water, and dried in vacuo. Recrystallization may be accomplished from methanol.

EXAMPLE 29

Comparative Solubilities in pH 7.2 Buffer at 25°

Solubilities were determined by suspending an excess amount of the compound in approximately 0.15 molar phosphate buffer (pH 7.2) and shaking overnight in a water bath at 25° to give a saturated solution. The concentration of the compound in the filtered solution was calculated on the basis of spectrophotometric measurements, i.e. comparison of the ultraviolet absorbance at the $\lambda_{max}$ for the saturated solution with the absorbance value observed for a known concentration of the compound. The results were summarized as follows:

| Compound | Solubility (mg/ml) |
| --- | --- |
| Acycloguanosine | 1.3–1.5 |
| Compound of Formula I | 3.6 |

| Compound | Solubility (mg/ml) |
|---|---|
| Compound of Formula II | 2.8 |

EXAMPLE 30

Phosphorylation of Compounds of Formula I and II and of Acycloguanosine by Herpes virus-induced Thymidine Kinase 30 μg of compound of formula I dissolved in 30 μl of 50% dimethylsulfoxide (DMSO) were incubated in a final volume of 150 μl for 3 hours at 37° C. with 50 mM Tris-HCl buffer, pH 7.5, 2.5 mM adenosine triphosphate, 2.5 mM magnesium chloride,. 7.5 mM phosphocreatine, 2 units of creatine kinase, 2 mM dithiothreitol, 2.5 mM sodium fluoride, 50 μg of bovine serum albumin and 0.0014 units of thymidine kinase, isolated from virus-infected HeLa cells (HSV1 virus), at a multiplicity of 10, (10 virus particles per cell), harvested 8 hours post infection) by the method of CHENG & OSTRANDER (Journal of Biological Chemistry, 1976, vol. 251, p 2605).

Two similar mixtures, one containing 30 μg of compound of formula II and the other 30 μg of acycloguanosine, both in 50 % DMSO were similarly treated.

A fourth mixture, similar to the above but containing only 30 μl of 50% DMSO and no anti-viral compound was also treated similarly as a control.

At the end of the 3 hour incubation period, 10 μl samples of each of the mixtures were analyzed by HPLC using an AX-10 column and a potassium phosphate ($KH_2PO_4$) gradient elution (0.01 to 1.0M). The amount of the monophosphate derivative of each anti-viral compound was estimated by integration of the area under the respective chromatographic peaks. The results indicated that 16% of acycloguanosine was converted to the monophosphate derivative while 90% of compound of formula I and 95% of compound of formula II were converted to the respective monophosphates under the same conditions.

To the rest of the incubation mixtures were now added 0.04 units of guanosine monophosphate kinase and 20 μl of an extract of HSV1-infected HeLa cells [The cells were infected with the virus at a multiplicity of 10 and harvested 8 hours later; they were suspended in a solution containing 0.35M $KH_2PO_4$, pH 7.5, 0.5 mM dithiothreitol, 0.2% polyoxyethylene(9)octylphenol (Nonidet P-40), 14% glycerol at 50 mg/ml and after 30 minutes at 4° were centrifuged at 100,000 mg; the supernatant liquid was the crude extract.] Incubation was continued at 30° for 4 more hours, after which samples were analyzed by HPLC and the amount of the triphosphate derivatives of each compound determined by integration of the area under the respective chromatographic peak. The results indicated that 31% of acycloguanosine was converted to the triphosphate under these conditions as compared to a conversion of 55% of compound of formula I and 93% of compound of formaul II to the respective triphosphate derivatives.

Since phosphorylation is presumed to be a prerequisite for the anti-viral activity of these compounds, the higher rate of phosphorylation of compounds of formula I and II to the monophosphate and triphosphate derivatives represents a considerable improvement over acycloguanosine.

EXAMPLE 31

Enzymatic Preparation of the Acyclic Monophosphate of Compound of Formula II

The compound of formula II (25 mg) was incubated at 37° in a mixture containing: 50 mM potassium phosphate buffer at pH 6.5; bovine serum albumin, 1 mg/ml; adenosine triphosphte, 5 mM; magnesium chloride,, 5mM; dithiothreitol, 1 mM; phosphocreatine, 1 mM; creatine kinase, 12.5 units/ml; sodium fluoride, 2.5 mM; and 500 units of purified HSV1-induced thymidine kinase, in a total volume of 10 ml. The progress of the reaction was monitored by high performance liquid chromatography (HPLC). When 35% of compound II had been converted to the monophosphate, the reaction was terminated. The product was purified by HPLC chromatography on a preparative anion exchanged column (AX-10, Varian) and desalted by chromatography on diethylaminoethyl cellulose (DEAE) with triethylammonium carbonate pH 7.6 as the eluting solvent. Freeze-drying of the solvent from the pooled fractions containing the product yielded 8 mg of compound of formula II monophosphate, the purity of which was confirmed by analytical HPLC.

EXAMPLE 32

Enzymatic Preparation of the Diphosphate of Compound of Formula II

The compound of formula II (20 mg) was incubated at 37° in a 10 ml mixture containing: 50·mM potassium phosphate buffer at pH 6.5; bovine serum albumin, 1 mg/ml; adenosine triphosphate, 5 mM; magnesium chloride, 5 mM; dithiothreitol, 1 mM; phosphocreatine 1 mM; creatine kinase, 12.5 units/ml; sodium fluoride, 2.5 mM; 500 units of purified HSV1-induced thymidine kinase and 100 μg of guanosine monophosphate kinase from hog brain. The progress of the reaction was monitored by high performance liquid chromatography (HPLC). The incubation was continued for 4 hours at 37° C and 20 hours at 30°. The pyrophosphate product was purified by HPLC chromatography on a preparative anion exchange column (AX-10, Varian) and desalted by chromatography on diethylaminoethyl cellulose (DEAE) with triethylammonium carbonate, pH 7.6 as the eluting solvent. Freeze-drying of the solvent from the pooled fractions containing the product yielded 10 mg of compound of formula II diphosphate, the purity of which was confirmed by analytical HPLC.

EXAMPLE 33

Enzymatic Conversion of the Diphosphate of Compound of Formula II to the Linear Triphosphate The diphosphate of compound of formula II (5 mg), prepared as in Example 23, was incubated at 37° in a 5 ml mixture containing: Tris-acetate buffer, pH 7.6, 50 mM; magnesium chloride, 3 mM; ethylenediamine tetraacetic acid (EDTA) and 1 mM; potassium phosphate, pH 7.5, 30 mM; pyruvate, 5 mM; glyceraldehyde phosphate, 30 mM; lactic dehydrogenase, 150 μg; glyceraldehyde phosphate dehydrogenase, 150 μg; 3-phosphoglycerate kinase, 150 μg; and nicotinamide adenine dinucleotide (NAD+), 15 mM. The progress of the reaction was monitored by high performance liquid chromatography (HPLC). Incubation was continued for 4 hours at 37° and 20 hours at 30°. The product was isolated by HPLC chromatography on an anion exchange column (AX-10, Varian) and desalted by chromatography on diethylaminoethyl cellulose (DEAE), with triethylammonium carbonate, pH 7.6 as the eluting solvent. Freeze-drying of the pooled fractions containing the product yielded 4 mg of the triphosphate of compound of formula II, the purity of which was confired by analytical HPLC.

EXAMPLE 34

Enzymatic Preparation of the Triphosphate of Compound of Formula II

The compound of formula II (20 mg) was incubated at 37° in a 10 ml mixture containing: Tris-HCl, pH 7.5, 50 mM; magnesum chloride, 2.5 mM; adenosine-5'-triphosphate, 2.5 mM; bovine serum albumin, 500 mg/ml; dithiothreitol, 2 mM; phosphocreatine, 7 mM; creatine kinase, 12.5 units/ml; sodium fluoride, 2.5 mM; HSV1-induced thymidine kinase, 400 units; and guanosine monophosphate kinase, 80μg. Incubation was continued for 4 hours at 37° and for 20 hours at 30°. The progress of the reaction was monitored by analytical high performance liquid chromatography. The product was isolated by HPLC chromatogrphy on a preparative anion-exchange column (AX-10, Varian) and then re-chromatographed on an analytical column, (Zorbax-NH$_2$) to remove contaminating ATP. The product was desalted by chromatography on diethylaminoethyl cellulose (DEAE) with triethylammonium carbonate pH 7.6 as the eluting solvent. Freeze-drying of the pooled fractions containing the product yielded 15 mg of the triphosphate derivative of compound of formula II, the purity of which was confirmed by analytical HPLC.

EXAMPLE 35

Competition Between Thymidine and Acycloguanosine or Compound of Formula II for Phosphorylation by the Virus-Induced Thymidine Kinase (1) 20 μg of acycloguanosine dissolved in 20 μl of 50% DMSO was incubated in a total volume of 120 μl (0.75 mM) with 80 mM Tris-HCl, pH 7.5, 4 mM adenosine triphosphate, 4 mM magnesium chloride, 1.7 mM dithiothreitol, 12.5 mM phosphocreatine, 5.0 mM sodium fluoride, 100 μg bovine serum albumin, 2.5 units of creatine kinase and 0.006 units of thymidine kinase, isolated from HSV1-infected HeLa cells (as per Example 22). Incubation was carried out at 37° for 2 hours and then continued at 30° for 18 hours.

(2) A second mixture containing the same ingredients as mixture No. 1 plus 2.5 mM thymidine was incubated in the same manner.

(3) A third mixture containing the same ingredients as mixture No. 1 but with 20 μg of compound of formula II replacing the acycloguanosine was incubated in the same manner.

(4) A fourth mixture containing the same ingredients as mixture No. 3 plus 2.5 mM thymidine was incubated in the same manner.

At the end of the incubation the amount of each antiviral compound converted to the corresponding monophosphate derivative was determined after HPLC analysis by integration of the area under the chromatographic peaks (column and elution conditions as in Example 22).

The percent of monophosphate present at the end of incubation in the four mixtures was as follows:

| Mixture No. | Compounds present | Percent monophosphate |
| --- | --- | --- |
| 1 | Acycloguanosine | 27 |
| 2 | Acycloguanosine & Thymidine | 0 |
| 3 | Compound of Formula II | 93 |
| 4 | Compound of Formula II & Thymidine | 23 |

The results indicated that compound of formula II is phosphorylated by the viral thymidine kinase even in the presence of a large excess of thymidine whereas acycloguanosine was not phosphorylated at all under the same conditions. Since phosphorylation is a prerequisite for the anti-viral activity of these compounds and since thymidine is a normal constituent of the cells, the compound of formula II represents a significant improvement over acycloguanosine.

EXAMPLE 36

Comparison of the Kinetic Parameters of Acycloguanosine and Compound of Formula II with Purified Viral Thymidine Kinase A series of mixtures containing in a total volume of 100 μL: 22 μmoles potassium phosphate buffer at pH 6.5; 0.3 μmoles MgCl$_2$; 0.5 μmoles of adenosine triphosphate; 100 μg of bovine serum albumin; 20 unis of HSV1-induced thymidine kinase and varying amounts of either compound of formula II or acycloguanosine, labeled with radioactive carbon ($^{14}$C) at position 8 of the guanine ring were incubated for 15 minutes at 37°. At the end of this period, 80 μL aliquots from each tube were applied to circular filter papers (2.5 cm diameter) of diethylaminoethyl cellulose (Whatman DE81). Five minutes later, the filters were placed into a beaker with water and washed successively once with water, twice with 50% ethanol containing 0.5 mM guanosine, and once with absolute ethanol. They were then placed in scintillation vials, dried in a stream of air, and counted in a scintillation counter after addition of scintillation mixture (Aquasol 2, New England Nuclear). By this procedure, unphosphorylated compounds were washed away and only phosphorylated derivatives adhered to the DE81 filters; thus the radioactivity counted was a measure of the conversion of the substrates, compound of formula II or acycloguanosine, to their phosphorylated derivatives by the action of the viral thymidine kinase. Proper controls for background radioactivity were included in the assays and used to correct the results.

The number of moles of phosphorylated derivatives present in each assay tube at the end of the incubation period was calculated from the number of counts of radioactivity measured for each filter and the specific activity (counts per minute per mole) of each substrate in the assay mixtures. The data were plotted in a graph of reaction velocity versus substrate concentration. FIG. 1 is a graph of the computer-generated theoretical curves best fitting the actual experimental data. The curve obtained in a similar experiment with thymidine as the substrate is included in FIG. 1 for comparison.

The kinetic parameters $K_m$, $V_{max}$ and $V_{max}/K_m$ for the two substrates were computed from the same data. The values obtained by averaging three separate experiments like the one described above were as follows:

|  | Compound of Formula II | Acycloguanosine |
|---|---|---|
| $K_m(\mu M)$ | 66 | 426 |
| $V_{max}$(pmoles/min) | 280 | 61 |
| $V_{max}/K_m$ | 4.25 | 0.14 |

Inasmuch as the ratio $V_{max}/K_m$ is the most commonly used measure for comparing substrate efficiencies, the relative efficiencies of compound of formula II and acycloguanosine as substrates for the HSV1-induced thymidine kinase are 4.25 to 0.14 or 30 to 1.

EXAMPLE 37

Comparison of the Kinetic Parameters of Acycloguanosine and Compound of Formula II with Purified Guanosine Monophosphate Kinase A series of mixtures containing in a total volume of 700 μl: 70 μmoles Tria-acetate buffer at pH 7.6; 70 μmoles KCl; 7 μmoles MgCl₂; 2.8 μmoles ATP; 1.05 ‖ moles phosphoenolpyruvate; 175 μg bovine serum albumin; 0.15 μmoles reduced nicotinamide-adenine dinucleotide (NADH); 3 units lactic dehydrogenase; 1.5 units pyruvate kinase; and varying amounts of either acycloguanosine monophosphate or the monophosphate of compound of formula II are incubated at 25° with guanosine monophosphate kinase from hog brain (Boehringer-Mannheim) in the cuvette of a Cary spectrophotometer recording the absorbance at 340 nm. In this coupled spectrophotometric assay the rate of phosphorylation of the monophosphate substrates to the corresponding diphosphates is calculated from the decrease in absorbance at 340 nm of the NADH. Since acycloguanosine monophosphate is a much poorer substrate for the kinase than compound of formula II monophosphate, more enzyme is used in the case of acycloguanosine monophosphate (0.28 units) than in the case of compound of formula II monophosphate (0.0056 units).

The initial velocities obtained in the above experiment are used to compute the kinetic parameters of the two substrates which are presented in the following table. The parameters obtained in a similar experiment for deoxyguanosine monophosphate are included for comparison:

|  | Compound of Formula II Monophosphate | Acycloguanosine monophosphate | Deoxyguanosine monophosphate |
|---|---|---|---|
| Km(μM) | 22 | 316 | 124 |
| $V_{max}$ (μg/min/mg) | 7.1 | 0.20 | 17.2 |
| $V_{max}/Km$ | 0.32 | 0.00065 | 0.14 |

The relative efficiency of compound of formula II monophosphate and acycloguanosine monophosphate as substrates for the enzyme which converts them to the respective diphosphates is 0.32/0.00065 or 492 to 1.

EXAMPLE 38

Enzymatic Preparation of the Acyclic Monophosphate of Compound of Formula I

The compound of formula I (1 mg) was incubated at 37° in a mixture containing: 50 mM potassium phosphate buffer at pH 6.5; bovine serum albumin, 1 mg/ml; adenosine triphosphate, 5 mM magnesium chloride, 5 mM; dithiothreitol, 1 mM; phosphocreatine 1 mM; creatine kinase, 12.5 units/ml; sodium fluoride, 2.5 mM; and 20 units of purified HSV1-induced thymidine kinase, in a total volume of 0.5 ml. The progress of the reaction was monitored by high performance liquid chromatography (HPLC). When 65% of the compound of formula I had been converted to the monophosphate, the reaction was terminated. The product was purified by HPLC chromatography on a preparative anion exchange column (AX-10, Varian) and desalted by chromatography on diethylaminoethyl cellulose (DEAE) with triethylammonium carbonate pH 7.6 as the eluting solvent. Freeze-drying of the solvent from the pooled fractions containing the product yielded 500 μg of compound I monophosphate, the purity of which was confirmed by analytical HPLC.

EXAMPLE 39

Treatment of Virus Infections in Cell cultures in Vitro

Assays were performed in various cell culture systems to determine the minimum concentrations of the compounds of formula I, formula II or acycloguanosine that were effective in preventing several different kinds of virus infections. The assays are described below and results are presented in Table I.

a. Herpes simplex virus types 1 and 2

The compounds of formula I, formula II or acycloguanosine required to totally suppress the development of viral cytopathology in 50% of rabbit kidney cell monolayers infected with 10 tissue culture infectious doses (TCID₅₀) of either virus were determined. All three compounds showed comparable activity.

b. Varicella-Zoster virus

Both the compound of formula II and acycloguanosine were equally active against this herpesvirus as determined by a plaque-reduction assay using monolayers of human fetal diploid lung cells, MRC-5.

c. Epstein-Barr virus (EBV)

Continuous treatment of EBV-infected umbilical cord cells (B lymphocytes) with 1-5 μg/ml of the compound of formula II from the time of infection resulted in inhibition of the transformation of the normal lymphocytes into continuously growing lymphoblastoid cells. By contrast, between 10 and 100 μg/ml of acycloguanosine were required to show similar activity.

d. Cytomegalovirus

The compound of formula II was effective in suppressing cytomegalovirus plaque formation on MRC-5 cell monolayers using 0.1 to 0.6 μg/ml. In order to obtain equivalent plaque suppression (50%) using acycloguanosine required 2.2–17.7 μg/ml. The calculated average relative potency of the compound of formula II to acycloguanosine (95% CI) was 28.6.

TABLE I

Minimum Concentrations of Formula I, Formula II or Acycloguanosine Active Against Hervesviruses in Cell Cultures

| Virus | Minimum Effective Concentration (μg/ml) | | |
|---|---|---|---|
| | Formula I | Formula II | Acyclo-guanosine |
| Herpes simplex type 1 (Strain Schooler) | 1–3[a] | 1–3[a] | 1–3[a] |
| Herpes simplex type 1 (Strain S) | ND | 1–3[a] | ND |
| Herpes simplex type 1 (Strain McIntyre) | ND | 3[a] | ND |
| Herpes simplex type 1 (Strain McKrae) | ND | 1–3[a] | ND |
| Herpes simplex type 2 (Strain Curtis) | 3–6[a] | 1–3[a] | 1–3 |
| Varicella-Zoster (Strain KMcC) | ND | 1–2[b] | 1–2[b] |
| Epstein-Barr (B95-8) | ND | 1–5[c] | 10–100[c] |
| Cytomegalovirus (Towne Strain) | ND | 0.1–0.6[d] | 2.2–17.7[d] |

ND — Not done
[a]Tube dilution assay on primary rabbit kidney cell cultures.
[b]Plaque reduction assay on human MRC-5 cell monolayers.
[c]Human cord blood lymphocyte transformation assay.
[d]Plaque reduction assay on human MRC-5 cell monolayers

EXAMPLE 40

Treatment of Herpes Simplex Virus Infection in Mice

Twenty gram ICR/Ha mice were injected intraperitoneally (ip) with 0.5 ml of a $10^{-5}$ dilution of a stock preparation of Herpes simplex virus type I (HSV-1), strain Schooler. This virus challenge infected each animal with approximately 100 LD$_{50}$. Starting immediately after virus infection and continuing twice daily for 4 days, each animal was injected subcutaneously in groups of 15 with: 500 μg, 125 μg or 31 μg of acycloguanosine; 500 μg, 125 μg, or 31 μg of the compound of formula I; 500 μg, 125 μg, or 31 μg of the compound of formula II; or placebo (physiological saline, pH 11.5). The placebo group was composed of 45 animals. All compounds were solubilized in physiological saline, pH 11.5.

The mice were observed daily for 15 days at the same time each day and the day of death was recorded for each animal.

Statistical analyses (reference: Liddel, F. D. K., 1978, Evaluation of Survival in Challenge Experiments, Microbiol. Rev., 42: 237-249) were performed on survival times transformed by the negative exponential transformation:

$$f(t) = 1 - (0.1)^{t/T}$$

where t = number of days an animal survived
T = duration of trial (15 days)

A continuity correction was used to account for daily observation:

$$f_c(t) = \tfrac{1}{2}[f(t) + f(t-1)]$$

Within each group, mice surviving through the trial period were assigned equally values of 0.9 and 1.0 to adjust for termination of the trial.

Average survival time per group was calculated from average corrected transformed survival times [$f_c(t)$] as follows:

$$t \text{ avg} = [T/\log(0.1)] \cdot [\log(1 - f_c(t))]$$

The summarized results are shown in Table II:

TABLE II

| Chemical Agent | Animal Treatment | | Percent Survival[a] | Avg. Survival Time (Days) |
|---|---|---|---|---|
| | μg/dose | mg/kg/day | | |
| Acycloguano-sine | 500 | 50 | 0 | 7.7 |
| | 125 | 12.5 | 6 | 6.2[b] |
| | 31 | 3.1 | 6 | 6.4[b] |
| Compound of Formula I | 500 | 50 | 60 | 11.8 |
| | 125 | 12.5 | 26 | 9.0 |
| | 31 | 3.1 | 0 | 6.3[b] |
| Compound of Formula II | 500 | 50 | 100 | 19.1 |
| | 125 | 12.5 | 73 | 14.1 |
| | 31 | 3.1 | 53 | 12.5 |
| Placebo | 0.1 ml | — | 6 | 6.2 |

[a] determined at 15 days
[b] values not statistically different from that of placebo treated animals (P ≥ 0.05)

EXAMPLE 41

Treatment of Herpes Simplex Virus Infection in Mice

The experiment described in Example 36 was repeated, except that each animal was injected twice daily subcutaneously in groups of 15 with: 1000 μg, 500 μg or 125 μg of acycloguanosine; 500 μg, 125 μg or 31 μg of the compound of formula I; 500 μg, 125 μg, 31 μg, 8 μg or 2 μg of the compound of formula II; or placebo. The 1000 μg dose acycloguanosine treatment group and the 500 μg dose treatment group of the compound of formula II were composed of 10 animals each. The summarized results are shown in Table III:

TABLE III

| Chemical Agent | Animal Treatment | | Percent Survival[a] | Avg. Survival Time (Days) |
|---|---|---|---|---|
| | μg/dose | mg/kg/day | | |
| Acycloguano-sine | 1000 | 100 | 10 | 7.8 |
| | 500 | 50 | 0 | 7.8 |
| | 125 | 12.5 | 6 | 7.0[b] |
| Compound of Formula I | 500 | 50 | 36 | 10.5 |
| | 125 | 12.5 | 33 | 9.8 |
| | 31 | 3.1 | 6 | 7.2[b] |
| Compound of Formula II | 500 | 50 | 100 | 19.5 |
| | 125 | 12.5 | 93 | 17.2 |
| | 31 | 3.1 | 46 | 11.8 |
| | 8 | 0.8 | 40 | 9.8 |
| | 2 | 0.2 | 26 | 9.0 |
| Placebo | 0.1 ml | — | 0 | 6.3 |

[a]determined at 15 days
[b]values not statistically different from that of placebo treated animals (P ≥ 0.05)

Using combined results from Examples 36 and 37, the calculated average relative potencies of the compound of formula I and the compound of formula II to acycloguanosine (95% CI) were 9.2 and 287.0, respectively.

EXAMPLE 42

The following is a summary of in vitro and in vivo antiviral activities of potassium 9-(1,3-dihydroxy-2-propoxymethyl)guanine cyclic monophosphate against Herpes simplex virus Type 1 (HSV1) and Type 2 (HSV2).

IN VITRO ASSAYS

Method

Confluent monolayers of primary rabbit kidney cell cultures were refed with maintenance medium containing serial dilutions of the test compounds and incubated overnight at 37°. At each dilution, four cultures were challenged with approximately 10 $TCID_{50}$ HSV1, four cultures were challenged with approximately 10 $TCID_{50}$ HSV2 and two cultures were left as toxicity controls. Cultures were reincubated at 37° and observed for viral induced cytopathology at days 5 and 7.

| Compound | Min. Effective Dose ($\mu$g/ml) Against | | |
|---|---|---|---|
| | HSV1 | HSV2 | Toxicity |
| Potassium 9-(1,3-dihydroxy-2-propoxymethyl)guanine cyclic monophosphate | 12.5–25 | 50–100 | Not tox. at 100 |

IN VIVO ASSAYS

Method

Twenty gram ICR/Ha mice were infected with approximately 100 lethal doses ($100LD_{50}$) of HSV1 (Strain Schooler) by the intraperitoneal route. Groups of 10 infected animals were treated twice daily for four days starting immediately after infection by subcutaneous injection at final daily doses of 50, 12.5, 3.1, 0.8, 0.2, 0.05 and 0.0125 mg/kg of potassium 9-(1,3-dihydroxy-2-propoxymethyl)guanine cyclic monophosphate. The mice were observed daily for 15 days at the same time each day and the day of death recorded for each animal. Average survival times (days) and percent survival at 15 days are shown in Table IV.

TABLE IV

| Compound | Animal Treatment mg/kg/day | Percent Survival | | Ave. Survival Time (days) | |
|---|---|---|---|---|---|
| | | Expt. 1 | Expt. 2 | Expt. 1 | Expt. 2 |
| Potassium 9-(1,3-dihydroxy-2-propoxymethyl)guanine cyclic monophosphate | 50 | 100 | ND | 19.5 | ND |
| | 12.5 | 100 | 60 | 19.5 | 15.0 |
| | 3.1 | 20 | 50 | 10.7[a] | 11.5 |
| | 0.8 | 40 | 0 | 10.5[a] | 7.4[a] |
| | 0.2 | 70 | 30 | 13.5 | 8.3[a] |
| | 0.05 | ND | 0 | ND | 6.0[a] |
| | 0.0125 | ND | 10 | ND | 6.3[a] |
| Placebo | 0.1 ml | 20 | 10 | 7.8 | 6.4 |

[a]Values not statistically different from that of placebo treated animals (P $\geq$ 0.05) calculated for survival times.

Conclusion: Potassium 9-(1,3-dihydroxy-2-propoxymethyl)guanine cyclic monophosphate has demonstrated significant antiviral activity against Herpes simplex viruses in vitro and in vivo.

EXAMPLE 43

Comparative Data On Potassium 9-(1,3-dihydroxy-2-propoxymethyl)guanine cyclic monophosphate (hereinafter referred to as Cyclic Monophosphate)

A. In vitro: Antiviral Activities of Cyclic Monophosphate in Cell Culture Systems Assays were performed using a variety of cell culture systems to establish the effective antiviral dose, $ED_{50}$ ($\mu$g/ml), determined as the drug concentration required to inhibit the development of viral plaques by 50% of the number developed in untreated virus controls. $ED_{50}$ values developed for the cyclic monophosphate are compared on a weight basis to those established for the compound of Formula II and acyclovir. See Table II for results.

Conclusions:

(1.) The cyclic monophosphate was less active than either the compound of Formula II or acyclovir against herpes simplex virus infection. This difference varied from 5 to 30-fold.

(2.) The cyclic monophosphate was equipotent to the compound of Formula II against human cytomegalovirus, strain $AD_{169}$. Both compounds were approximately 10-fold more active than acyclovir.

(3.) The cyclic monophosphate was approximately 10-fold more active than either the compound of Formula II or acyclovir against Varicella-Zoster virus, strain KMcC.

(4.) The cyclic monophosphate was active ($ED_{50}$ approximately 1 $\mu$g/ml) against two animal herpes viruses tested, equine herpes virus and feline rhinotracheitis virus (data not shown). (5.) The cyclic monophosphate was inhibitory for each of the DNA viruses tested, (vaccinia, $SV_{40}$ and adenovirus), but was not effective against RNA virus replication (influenza A, vesicular stomatitis, and polio).

TABLE V

| | In vitro Antiviral Efficacy ($\mu$g/ml)[1] for 50% Inhibition of Plaque Formation | | | | | |
|---|---|---|---|---|---|---|
| Antiviral Compound | Herpes simplex Virus | Cytomegalo-Virus | Varicella Zoster Virus | Vaccinia | $SV_{40}$ | Adeno Type 2 |
| Cyclic Monophosphate | 3–6 | 0.8 | 0.4–0.8 | 6–12 | 6 | 3 |
| Compound of Formula II | 0.2 | 0.8 | 3–6 | 50–100 | NA | 50 |
| acycloguanosine | 0.2–0.4 | 25 | 3–6 | NA | ND | ND |

[1]Concentration required for 50% plaque inhibition.
NA = not active at 100 $\mu$g/ml
ND = not done The following cell culture systems were used in the work shown in Table V:

Herpes simplex virus, cytomegalovirus and varicella zoster virus, and vaccinia were assayed on MRC5 (human diploid lung) cell cultures.

$SV_{40}$ was assayed on CV-1 (monkey) cell cultures.

Adeno Type 2 was assayed on BSC (monkey) cell cultures.

B. In vivo: Antiviral Activites of Cyclic Monophosphate Against Herpes Simplex Virus Animal Model Infection Systems.

1. Animal Model Systems Evaluated.

Model herpes infection systems have been established to simulate clinical herpetic infection.

a. Intraperitaneal HSV-1 infection in mice results in a systemic infection with involvement of liver and spleen, viremia and eventually the central nervous system. Animals develop encephalitis. Drug efficacy given by oral gavage is evaluated by extension of animal survival time compared to placebo treated animals. Animals are challenged with 50 to 100 lethal equivalent doses of HSV-1 ($5-10\times 10^2$ plaque forming units).

b. A direct encephalitis can be established by intracerebral HSV-1 inoculation. This model infection is used to determine whether drug delivered parenterally can effectively cross the blood-brain barrier. Infection is in weanling mice for ease of intracerebral inoculation. Drug efficacy, given subcutaneously, is measured by extension of animal survival time.

c. HSV-1 orofacial infection of hairless mice results in a localized acute herpetic infection, with the classic progression from raised erythematous area through ruptured blisters to scab formation. The majority of infected mice survive and harbor latent ganglionic infection, which can be activated by removal and co-cultivation of the trigeminal ganglia from HSV-1 infected mice. Drug evaluation is based on prevention of development of local orofacial lesions, at a time of maximum involvement in placebo-treated infected mice (7 days after infection). This model has been used to evaluate both orally and topically applied drug.

d. HSV-2 vaginal infection in mice is progressive from local acute infection of the genital area to limb paralysis and eventual death. This is a consistent, reproducible model, but is more virulent and progressive than the human genital disease. Drug efficacy is determined ultimately by extension of animal survival time, and also by the limitation of progression of disease from acute local through paralysis to death. Animals are challenged using in excess of 10 lethal equivalent doses of HSV-2. This model was used to evaluate dosing by oral gavage.

e. Infection of rabbit eyes with HSV-1 results in punctate and/or dendritic herpetic corneal lesions within 3 days. Infection progresses to involve greater than 80% of the corneal surface and progresses to deeper stromal involvement within 6 to 8 days in untreated rabbits. Some animals eventually succumb to encephalitis. Drug efficacy is evaluated by suppression of corneal and stromal lesion development compared to placebo-treated infected animals. Drugs were delivered by eye drops applied 5 times daily. Lesion severity was evaluated by slit lamp microscopy daily prior to drug treatments.

The data summarized in Table VI were determined from dose response drug titrations. Minimum effective dose is determined as the dose which results in a significant increase in survival time or a significant decrease in local lesion severity compared to placebo-treated animals. Treatments were initiated within 3 hours of infection for intraperitoneal, intracerebral, orofacial and vaginal infections. Treatments of corneal HSV-1 infection of rabits were initiated 3 days after infection, a time at which herpetic lesions were evident.

See Table VI for results.

TABLE VI

Comparative In vivo Efficacy of Cyclic Monophosphate and Acyclovir Against Herpes Simplex Infections

| Virus | Infection Regimen[1] Route | Treatment[2] Regimen | Min. Effective Dose[3] Cyclic Phosphate | Acyclovir |
|---|---|---|---|---|
| HSV-1 | Intraperitoneal | oral | 0.8–3.1 | 12.5–50 |
| HSV-1 | Intracerebral | Subcutaneous | 0.8 | 50 |
| HSV-1 | Orofacial | Oral | 3.1 | 12.5 |
| HSV-1 | Orofacial | Topical | 0.06% | 0.25–1.0% |
| HSV-1 | Corneal | Topical | 1.0% | 1.0% |
| HSV-2 | Vaginal | Oral | 0.8 | 12.5–50 |

[1]Intraperitoneal and orofacial infections were in ICR/Ha and HRS mice using HSV-1. Corneal infection was in rabbits. HSVC-2 vaginal infection was in ICR/Ha mice. HSV-1 intracerebral infection was in ICR/Ha weanling mice.
[2]Oral treatments were by oral gavage twice daily for up to 10 days using drug solubilized in phosphate buffered saline. Topical treatments used drug solubilized in a hydroalchlolic vehicle for orofacial application 4 times daily or as ophthalmic drops applied 5 times daily.
[3]Minimum effective dose for oral and subcutaneous treatments of intraperitoneal, intracerebral, and vaginal infections was measured as mg/kg/day sufficient to effect significant increase in survival time compared to placebo-treated mice. For oral treatment of orofacial infection, minimal effective dose was measured as mg drug/kg/day sufficient to significantly decrease lesion severity (lesion size on a graded scale from no detectable lesions to total orofacial involvement) comparedto placebo-treated mice. For topical teatments, the minimum effective dose was the percent of drug applied which resulted in a significant decrease in lesion severity.

TABLE VII

Therapeutic Efficacy of Cyclic Monophosphate Against Vaginal HSV-2 Infection of Mice

| Antiviral Compound | Treatment[1] Initiation (hrs) | Survivors/ Total | Avg. Survival Days (confidence interval) |
|---|---|---|---|
| Cyclic Monophospate | 0 | 8/10[a] | 22.3[a] (17.1, 35.8) |
|  | 24 | 3/10 | 14.9[a] (11.8, 19.5) |
|  | 48 | 2/10 | 12.4[a] (9.6, 16.5) |
|  | 72 | 3/10 | 14.0[a] (10.5, 19.7) |
| Acyclovir | 0 | 1/10 | 8.0 (5.6, 11.2) |
|  | 24 | 3/10 | 12.1 (8.8, 17.3) |
|  | 48 | 5/10 | 12.4 (8.2, 20.7) |
|  | 72 | 1/10 | 9.0 (7.1, 11.3) |
| Placebo | 0 | 2/10 | 9.2 (6.6, 13.0) |

[a]significantly different ($p < 0.05$) than placebo-treated mice
[1]Treatment was initiated at the time indicated after infection, using 0.55 μmoles of Cyclic Monophosphate or acyclovir in 0.1 ml PBS (phosphate buffered saline) given by oral gavage. Treatment was continued twice daily for 10 days.

2. Conclusions a. The Cyclic Monophospate was an effective anti-herpetic agent when used orally or topically in herpes model infections.

b. As determined by minimum effective dose, the Cyclic Monophosphate was consistently more efficacious than acyclovir against intraperitoneal, intracerebral, orofacial, and vaginal infections of mice. The Cyclic Monophospate and acyclovir were equally effective in limiting progression and resolving the corneal lesions of infected rabbits.

c. Although not shown in Table VI, the antiviral efficacy of the Cyclic Monophosphate in the herpes-mouse infection model tested was generally equivalent to that devloped using the compound of Formula II.

d. The Cyclic Monophosphate was therapeutically effective when treatment was initiated up to 72 hours after HSV-2 vaginal infection (see Table VII). Comparable treatments suing acyclovir were ineffective in altering the progression of vaginal infection to paralysis and death.

The Cyclic Monophosphate has consistently shown in vivo antiviral activity, as measured by minimum effective dose, comparable to that for the compound of Formula II; and consistently superior to that generated by acyclovir. By contrast, the Cyclic Monophosphate is about 10-fold less active than either the compound of Formula II or acyclovir against HSV infection in cell culture. Why the Cyclic Phosphate is so effective in vivo is as yet unexplained, but compared to the compound of Formula II and acyclovir, it is readily soluble, which may influence absorption and distribution to the tissues. Significantly, however, the Cyclic Monophosphate, is, surprisingly, substantially more effective than acyclovir or the compound of Formula II in vitro against Varicella Zoster virus. In view of the fact that the Cyclic Monophosphate appears to perform substantially better in vivo than in vitro it is expected that in the therapeutic use in mammals its comparative effectiveness would be even more substantial.

C. Mode of Action

As implied from the different antiviral specificities observed for the Cyclic Monophosphate and the compound of Formula II (e.g., enhanced activity of the Cyclic Monophosphate against Varicella-Zoster virus, vaccinia, $SV_{40}$ and adenoviruses), the Cyclic Monophosphate does not appear to function primarily as a prodrug for the compound of Formula II, but instead has an independent mechanism of antiviral activity(s).

Further evidence for this can be demonstrated by the following:

Biological Activities of the Cyclic Monophosphate are not Dependent on Viral Thymidine Kinase In vitro data 1. The in vitro antiviral activity of the compound of Formula II against HSV-1 was readily reversed by addition of thymidine e.g. $ED_{50}$ of the compound of Formula II was 0.8–1.6 µg/ml in the absence of thymidine and 25 µg/ml in the presence of 20 µg thymidine/ml, a greater than 15-fold reduction of antiviral activity. By contrast, addition of thymidine reduced that $ED_{50}$ by 2 to 4-fold for the Cyclic Monophosphate, from 12.5 µg/ml to 25–50 µg/ml.

2. An HSV-1 mutant resistant to the compound of Formula II, HSV-1 ($383_{R1}$), has been isolated from HSV-1 strain Schooler, HSV-1 ($383_{R1}$) is approximately 100-fold less susceptible to protection by the compound of Formula II, but only 4 to 8-fold less susceptible than wild type to the Cyclic Monophosphate.

HSV-1 ($383_{R1}$) has retained about 10–20% of the HSV-1 capacity to phosphorylate thymidine, but is incapable of phosphorylation of the Compound of Formula II.

The Cyclic Monophosphate and the compound of Formula II have been evaluated for antiviral efficacy against HSV-1 and HSV-1 ($383_{R1}$) in cell cultures deficient in cellular thymidine kinase (3T3TK$^-$) and in cell cultures transfected to carry herpes TK, (3T3 TK$^-$/TK$^+_{HSV}$). The results are shown in Table VIII.

As indicated by the previously described biochemical studies, the antiviral activity of the compound of Formula II is dependent on expression of viral TK. The compound of Formula II is equally effective against HSV-1 infection of 3T3 TK$^-$ or 3T3 TK$^-$/TK$^+$ HSV cells or against HSV−1 ($383_{R1}$) in 3T3 TK$^-$/TK$^+$ HSV cells ($ED_{50}=0.06$ µg/µl), but is 100-fold less active against HSV−1 ($383_{R1}$) in 3T3 TK$^-$ cells ($ED_{50}=5.0$ µg/ml).

By contrast, the antiviral activity of the Cyclic Monophosphate is equivalent against HSV−1 ($383_{R1}$) on either 3T3 TK$^-$/TK$^+_{HSV}$ cells or on 3T3 TK$^-$ cells. Although the susceptibility of HSV−1 to the Cyclic Monophosphate is about 5-fold greater than is HSV−1 ($383_{R1}$), this difference does not correlate with the presence of viral TK.

In vivo Data

1. Similar relative efficacies of the Cyclic Monophosphate and the compound of Formula II have been observed for protection of mice against intraperitoneal infection with HSV−1 or HSV−1 ($383_{R1}$). Groups of mice infected intraperitoneally with increasing doses of HSV−1 or HSV−1 ($383_{R1}$) were treated twice daily subcutaneously for 4 days with either the Cyclic Monophosphate or the compound of Formula II. Mean survival times of treated mice were compared. There was no significant difference in protective efficacy of either drug against a $10^6$-fold virus challenge range, e.g. protection could not be overwhelmed by increased virus challenge.

However, the efficacy of the compound of Formula II was significantly lower against resistant mutant HSV−1 ($383_{R1}$) then against wild type HSV−1 (see Table IX). By contrast, the Cyclic Monophosphate was equally effective against either HSV−1 or HSV−1 ($383_{R1}$) and equally as effective as the compound of Formula II against HSV−1.

TABLE VIII

Viral Thymidine Kinase Independence for L648,164 Antiviral Efficacy In vitro

| | Antiviral Concentration (mg/ml)[2] | | | |
| --- | --- | --- | --- | --- |
| | Compound of Formula II | | Cyclic Monophosphate | |
| Host[1] Cell | HSV-1 WT | HSV-1 $383_{R1}$ | HSV-1 WT | HSV-1 $383_{R1}$ |
| 3T3 TK$^-$ | 0.06 | 5.0 ↑100× | 0.2 | 1.0 ↑1× |
| 3T3 TK$^-$/TK$^+_{HSV}$ | 0.06 | 0.06 | 0.2 | 1.0 |

[1]3T3 TK$^-$: NIH 3T3 mouse cells selected for absence of cellular thymidine kinase (TK)
3T3 TK$^-$/TK$^+_{HSV}$: 3T3 TK$^-$ cells transfected with HSV-1 TK gene.
[2]50% plaque reduction
HSV-1 WT: HSV-1 Schooler wild type.
HSV-1 $383_{R1}$: HLSV-1 Schooler selected for resistance to compound of Formula II as shown to be unable to phosphorylate the compound of Formula II to its monophosphate.

TABLE IX

In vivo Efficacy of Cyclic Monophosphate Against Infection by HSV-1 or HSV-1 ($383_{R1}$)

| Antiviral Compound | Mean Survival Time (± SD) | |
| --- | --- | --- |
| | HSV-1 | HSV-1 ($383_{R1}$) |
| Cyclic Monophosphate | 12.65 (0.84) | 13.42 (0.82) |
| Compound of Formula II | 12.55 (0.88) | 9.05 (0.80)[a] |

TABLE IX-continued

In vivo Efficacy of Cyclic Monophosphate
Against Infection by HSV-1 or HSV-1 (383$_{R1}$)

| Antiviral Compound | Mean Survival Time (± SD) | |
|---|---|---|
| | HSV-1 | HSV-1 (383$_{R1}$) |
| Placebo | 5.97 (0.43) | 7.35 (0.71) |

HSV-1: Wild Type HSV-1 (Schooler)
HSV-1 (383$_{R1}$): HSV-1 mutant resistant to Compound of Formula II
[a]Compound of Formula II was significantly less effective against HSV-1 (383$_{R1}$) than against HSV-1 (p < 0.0001)
However, Cyclic Monophosphate was equally effective against both viruses (p = 0.43)

III. Genetic Studies

Drug sensitivities of several HSV−1 and HSV−2 strains, altered by mutation in the DNA polymerase gene have been compared. In addition, by selection of intertypic recombinants of these HSV−1 and HSV−2 strains and fine mapping to determine the limits of the heterologous DNA polymerase genome inserts in the recombinants, a system useful for fine mapping drug resistance within the HSV DNA polymerase genone has been developed.

It has been determined that the region of the viral DNA polymerase genome involved in resistance to the compound of Formula II mapped separately from the region(s) involved in resistance to PAA, acyclovir and adenine arabinoside.

The same intertypic recombinants have been evaluated for sensitivity to the Cyclic Monophosphate, and the results are shown in Table X. Mutations in the DNA polymerase which produce an altered polymerase exhibiting resistance to PAA, acyclovir, and adenine arabinoside also appear to confer resistance to the Cyclic Monophosphate (e.g. R6-34, R6-19, PAA$^{R}$$_1$). However, HSV−2 Ts6, which is resistant to the compound of Formula II remains sensitive to PLAA, acyclovir, and the Cyclic Monophosphate.

The results indicate that the resistance to the Cyclic Monophosphate is closely linked to the region of the DNA Polymerase genome associated with resistance to PAA, acyclovir and adenine arabinoside. Furthermore, this region is distinct from the DNA sequences conferring resistance to the compound of Formula II.

This implies that the Cyclic Monophosphate exerts a part or all of its antiviral activity in a manner independent of the compound of Formula II and its phosphate derivatives synthesized in the living system.

TABLE X

Drug Sensitivities of HSV-1/HSV-2 Intertypic
Recombinants Within the Herpes DNA Polymerase Locus

| Virus | Sensitivity (S) or[1] Resistance (R) to | | ED$_{50}$ (μg/ml)[2] | |
|---|---|---|---|---|
| | PAA | Acyclovir | Compound of Formula II | Cyclic Monophosphate |
| Recombinant 6-26 | S | S | 0.05 | 1.1 |
| Recombinant 6-30 | S | S | 0.08 | 0.30 |
| Recombinant 6-34 | R | R | 0.07 | 6.3 |
| Recombinant 6-19 | R | R | 0.10 | 4.7 |
| HSV-1 PAA ®$_1$ | R | R | 0.10 | 3.2 |
| HSV-2 TS$_6$ | S | S | 15.5 | 0.40 |
| HSV-1 wild type Strain 17 | S | S | 0.34 | 0.90 |

[1,2]Sensitivity to phosphonoacetic acid (PAA) or Acyclovir was previously determined by drug titration to establish the concentration required to inhibit virus plaque fomation by 50% on vero cell monolayers.

IV. Conclusions

1. Both in vitro and in vivo efficacy experiments indicate that the antiviral activities of the Cyclic Monophosphate are independent of conversion to the compound of Formula II and that the Cyclic Monophosphate is not a significant prodrug for the compound of Formula II.

2. Mutations in the HSV DNA polymerase locus can confer resistance to either the compound of Formula II or the Cyclic Monophosphate independently. Resistance to the Cyclic Monophosphate appears to be linked closely to resistance to acyclovir, phosphonacetic acid and adenine arabinoside. These results imply that the inhibition of viral DNA polymerase is the result of different activated products of the compound of Formula II and the Cyclic Monophosphate.

EXAMPLE 44

Treatment of Herpes Simplex Virus Infection in Mice:
Intraperitoneal Herpes Simplex Type 1 Infection, Oral Treatment ICR/Ha mice were infected as described in Example 36. Groups of 10 infected animals were treated twice daily for 7 days by oral gavage at final daily doses of 100, 50, 12.5, 3.1 or 0.8 mg/kg of acycloguanosine, or 50, 12.5, 3.1, 0.8 or 0.2 mg/kg of the compound of formula II starting immediately after infection. In addition, two groups of five uninfected animals were treated with either acycloguanosine or the compound of formula II twice daily for 7 days by oral gavage at final daily doses of 50 mg/kg. These animals served as toxicity controls. The summarized results are shown in Table XI.

TABLE XI

Oral Treatment of
Intraperitoneal Herpes Simplex Virus
Type I Infection of Mice

| Chemical Agent | Animal Treatment | | Percent Survival[a] | Avg. Survival Time (days) |
|---|---|---|---|---|
| | mg/dose | mg/kg/day | | |
| Acycloguanosine | 1000 | 100 | 60 | 11.4 |
| | 500 | 50 | 20 | 8.2 |
| | 125 | 12.5 | 0 | 6.6[b] |
| | 31 | 3.1 | 0 | 6.3[b] |
| Compound of Formula II | 500 | 50 | 100 | 16.9 |
| | 125 | 12.5 | 80 | 13.9 |
| | 31 | 3.1 | 50 | 11.7 |
| | 8 | 0.8 | 20 | 8.5 |
| | 2 | 0.2 | 0 | 6.8[b] |
| Placebo | 0.1 | | 10 | 6.3 |

[a]determined at 13 days
[b]values not statistically different from that of placebo treated animals (P ≧ 0.05). Calculated for survival times only.

Treatment with the compound of formula II resulted in statistically significant extension of survival time compared to placebo-treated animals at 50, 12.5, 3.1 and 0.8 mg/kg daily doses. Acycloguanosine treatment resulted in statistically significant extension of survival time compared to placebo-treated animals only at 100 and 50 mg/kg daily doses.

All animals treated with 50 mg/kg of the compound of formula II survived the test; survival of the 50 and 12.5 mg/kg treatment groups was statistically significantly longer than the placebo-treated group. By contrast, none of the acycloquanosine-treated groups showed enhanced survival.

The relative potency of the compound of formula II to acycloguanosine was 50.3, which was statistically significant.

There was no evidence of overt toxicity in either the acycloquanosine or the compound of formula II treatment groups are measured by final weight of test animals.

EXAMPLE 45

Treatment of Herpes Simplex Virus Infection in Mice: Vaginal Herpes Simplex Virus Type 2 Infection, Oral Treatment Thirty gram ICR/Ha female mice were infected with more than 10 $LD_{50}$ of Herpes simplex virus type 2 (Strain Curtis) by the intravaginal route. Groups of 10 animals were treated twice daily for ten days by oral gavage using acycloquanosine or the compound of formula II at final daily doses of 50, 12.5, 3.1, 0.8 or 0.2 mg/kg starting immediately following infection. The average number of days to infection and the average days of survival were determined for each group and compared to an infected, placebo-treated group. The summarized results are shown in Table XII.

TABLE XII
ORAL TREATMENT OF VAGINAL HERPES SIMPLEX VIRUS TYPE II INFECTION OF MICE

| Chemical Agent | Animal Treatment μg/dose | mg/kg/day | Percent Survival[a] | Avg. Survival Time (days) |
|---|---|---|---|---|
| Acycloguanosine | 750 | 50 | 60 | 17.6 |
| | 188 | 12.5 | 40 | 14.1 |
| | 47 | 3.1 | 20 | 10.2[b] |
| | 12 | 0.8 | 10 | 10.1[b] |
| | 3 | 0.2 | 0 | 8.8[b] |
| The Compound of Formula II | 750 | 50 | 100 | 24.7 |
| | 188 | 12.5 | 100 | 24.7 |
| | 47 | 3.1 | 75 | 19.1 |
| | 12 | 0.8 | 40 | 15.1 |
| | 3 | 0.2 | 30 | 12.1[b] |
| Placebo | 0.1 ml | — | 0 | 9.3 |

[a] determined at 19 days
[b] values not statistically different from that of placebo treated animals (P ≧ 0.05); Calculated for survival times only All animals treated with the compound of formula II at 50 mg or 12.5 mg/kg survived the test; survival rates of the 50, 12.5 and 3.1 mg/kg the compound of formula II treatment groups were statistically significantly increased compared to the placebo-treated group. By contrast, only the 50 mg/kg acycloguanosine treatment group showed statistically significant enhanced survival.

The compound of formula II at 50, 12.5, 3.1 and 0.8 mg/kg resulted in a statistically significant increase in survival time compared to placebo-treated infected animals. Acycloguanosine at 50 and 12.5 mg/kg was similarly effective.

The relative potency of the compound of formula II to acycloguanosine as measured by survival was 28.1, which was statistically significant.

All animals treated with the compound of formula II at 50 mg/kg remained free of signs of herpetic infection for the duration of the test. The compound of formula II and acycloquanosine at both 50 mg/kg and 12.5 mg/kg resulted in statistically significant increases in the number of days to infection (development of vaginal lesions and/or paralysis) compared to placebo-treated animals.

The relative potency of the compound of formula II to acycloguanosine as measured by time to infection was 4.14, which was statistically significant.

EXAMPLE 46

Treatment of Herpes Simplex Virus Infection in Mice: Orofacial Herpes simplex Virus Type 1 Infection, Oral Treatment Twenty grams HRS (hairless) mice were infected on the abraded orofacial area with Herpes simplex virus type 1 (Strain S). Groups each composed of 10 infected animals were treated by oral gavage twice daily for 7 days starting 3 hours after infection using final daily doses of 50, 12.5, 3.1 and 0.8 mg/kg for acycloguanosine and 50, 12.5, 3.1, 0.8 and 0.2 mg/kg for the compound of formula II. At 7 days after initiation of infection, the extent of lesion development in the orofacial area was measured on a scale of 0 (no lesions) to 4 (massive lesions over the entire snout). Lesion incidence and average lesion scores are shown in Table XIII and in FIG. 2.

The compound of formula II treatment resulted in statistically significant protection at all concentrations used compared to placebo-treated infected animals when measured in terms of extent of lesion development. Acycloguanosine treatment resulted in statistically significant protection only at 50 and 12.5 mg/kg doses.

The compound of formula II treatment resulted in statistically significant protection at 50 and 12.5 mg/kg doses compared to the incidence in placebo-treated infected animals when measured in terms of incidence of lesions. By contrast, acycloguanosine treatment resulted in statistically significant protection only at 50 mg/kg.

The relative potency of the compound of formula II to acycloguanosine was 6.9, which was statistically significant.

TABLE XIII

| Chemical Agent | Animal Treatment μg/dose | mg/kg/day | Lesion Incidence Total | (%) | Lesion Severity[a] |
|---|---|---|---|---|---|
| Acycloguanosine | 500 | 50 | 1/7 | (14) | 0.14 |
| | 125 | 12.5 | 6/6 | (100)[b] | 2.67 |
| | 31 | 3.1 | 6/6 | (100)[b] | 3.25[b] |
| | 8 | 0.8 | 7/8 | (88)[b] | 3.11[b] |
| The Compound of Formula II | 500 | 50 | 1/10 | (10) | 0.05 |
| | 125 | 12.5 | 2/10 | (20) | 0.45 |
| | 31 | 3.1 | 6/9 | (67)[b] | 1.00 |
| | 8 | 0.8 | 7/7 | (100)[b] | 2.93 |
| | 2 | 0.2 | 7/7 | (100)[b] | 2.93 |
| Placebo | 0.1 ml | — | 10/10 | (100) | 3.95 |

[a] Lesion severity was measured on a scale of 0 (no lesions) to 4 (massive lesions over the entire orofacial area), with the average lesion score presented in this Table.
[b] Values not statistically differeat from that of placebo treated animals (P ≧ 0.05). Lesion incidence and severity were determined seven days following orofacial infection.

EXAMPLE 47

Treatment of Herpes Simplex Virus Infection in Mice: Orofacial Herpes simplex Virus Type 1 Infection, Therapeutic Oral Treatment Twenty gram HRS (hairless) mice were infected on the abraded orofacial area with Herpes simplex virus type 1 (Strain S).

a. Groups of 10 infected animals were treated twice daily by oral gavage for up to 7 days with the compound of formula II at 12.5 mg/kg/day, starting 3, 8, 12, 24, 48, 72, or 96 hours after infection.

b. In a second experiment, the therapeutic efficacy of acycloguanosine was evaluated in a similar manner. Groups of 10 infected animals were treated twice daily by oral gavage for up to 7 days with acycloguanosine at 12.5 mg/kg/day, starting at 3, 8, 12, 24, 48, 72, or 96 hours after infection.

At 7 days after initiation of infection, the extent of lesion development in the orofacial area was measured on a scale of 0 (no lesions) to 4 (massive lesions over the entire snout). Average lesion scores are shown in Table XIV.

Infected mice receiving the compound of formula II starting as late as 72 hours after infection with HSV-1 showed statistically significant lower lesion scores than mice receiving placebo. By contrast, for acycloguanosine treatment, only mice receiving treatment starting 3 hours after infection were statistically different in lesion score than the placebo group.

In addition, infected mice receiving the compound of formula II starting at 8, 12 and 24 hours after infection had a statistically significant lower incidence of lesion development than mice receiving placebo. None of the acycloguanosine treated groups had a significantly lower incidence of lesions than the respective placebo treated animals.

TABLE XIV

Therapeutic Oral Treatment of Orofacial Herpes Simplex Virus Type I Infection of Mice

| Chemical Agent | Start of Oral[a] Treatment (Hours post infection) | Lesion Incidence Total | (%) | Lesion Severity[b] |
|---|---|---|---|---|
| Acycloguanosine | 3 | 10/10 | (100)[c] | 2.80 |
| 12.5 mg/kg/day | 8 | 10/10 | (100)[c] | 2.95[c] |
| | 12 | 9/10 | (90)[c] | 3.30[c] |
| | 24 | 9/10 | (90)[c] | 2.85[c] |
| | 48 | 8/10 | (80)[c] | 2.85[c] |
| | 72 | 9/10 | (90)[c] | 3.60[c] |
| | 96 | 7/7 | (100)[c] | 4.00[c] |
| Placebo | 3 | 9/9 | (100) | 3.35 |
| The Compound of | 3 | 6/10 | (60)[c] | 1.30 |
| Formula II | 8 | 3/10 | (30) | 0.55 |
| 12.5 mg/kg/day | 12 | 5/10 | (50) | 0.55 |
| | 24 | 4/10 | (40) | 0.40 |
| | 48 | 9/10 | (90)[c] | 1.50 |
| | 72 | 8/10 | (80)[c] | 2.55 |
| | 96 | 10/10 | (100)[c] | 3.85[c] |
| Placebo | 3 | 10/10 | (100) | 4.00 |

[a]Oral treatment was started at the indicated times after initiation of infection and continued with dosing twice each day for seven days.
Lesion incidence and severity were determined seven days following orofacial infection.
[b]Lesion severity was measured on a scale of 0 (no lesions) to 4 (massive lesions over the entire orofacial area), with the average lesion score presented in this table.
[c]Values not statistically different from that of placebo treated animals (P ≧ 0.05).

Method of Preparing Phosphate Derivatives of Compounds of Formula I and II

The mono- and polyphosphate derivatives of compounds of Formulas I and II may be prepared chemically by reacting a compound of Formula I or II with a phosphorylating agent such as phosphoryl chloride in a suitable aprotic solvent such as triethyl phosphate and treating the resulting intermediate with water or base. The major product of this reaction is the cyclic phosphate of compound I or II, but acylic mono-diphosphates are also produced. The product ratios can be varied by changes in the amounts of the reactants or the length and temperature of treatment.

It is also convenient to isolate the phosphorylated intermediate by precipitation with a nonpolar hydrocarbon solvent and quench with an alcohol. The product of this reaction can be either an alkyl phosphodiester or an alkyl phosphotriester derivative depending upon whether a basic aqueous treatment is employed or not.

The phosphorylated derivatives of the compounds of formulas I and II [namely the mono, linear di(pyrophosphate), or linear tri-phosphate] can also be prepared enzymatically by treatment of the compound of formulas I or II with HSVI thymidine kinase (to produce the monophosphate), additionally with guanosine monophosphate kinase (to produce the pyrophosphate), and additionally with 3-phosphoglycerate kinase (to prepare the triphosphate).

What is claimed is:

1. A compound of the formula:

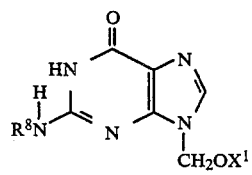

wherein $X^1$ is

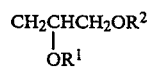 (I)

or

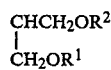 (II)

where
$R^1$ and $R^2$ are independently H or

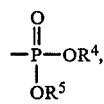

or $OR^1$ and $OR^2$ together are

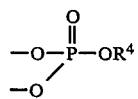

provided that $R^1$ and $R^2$ are never simultaneously H;
$R^4$ and $R^5$ are independently H, sodium, potassium, ammonium, $C_1$–$C_4$-alkyl-substituted-ammonium, magnesium/2, calcium/2, aluminum/3, $C_1$–$C_8$-straight or branched-chain alkyl, phenyl, phenyl-$C_1$–$C_4$-alkyl, phosphate or pyrophosphate; and
$R^8$ is H or

wherein $R^9$ is H; unsubstituted $C_1$–$C_{20}$-straight or branched-chain, saturated or mono- or polyunsaturated alkyl; unsubstituted or substituted phenyl, wherein the substituent(s) is/are independently halogen or $C_1$–$C_4$-alkyl; pyridyl; piperidyl; furyl; imidazolyl; tetrahydrofuryl; thienyl; phenyl-$C_1$-$C_4$-alkyl; $C_1$-$C_4$-alkoxy-$C_1$-$C_4$-alkyl; phenyloxy-$C_1$-$C_4$-alkyl; or when $X^1$ is the structure (I), alternatively also substituted $C_1$-$C_{20}$-straight or mono- or polyunsaturated alkyl, wherein the substituent(s) is/are independently hydroxy, amino, or carboxyl.

2. A compound according to claim 1, wherein $R^4$ is H.

3. A compound of Formula II of claim 1, wherein $R^1$ or $R^2$ is

and $R^2$ or $R^1$ is H.

4. The compound of claim 1 which is

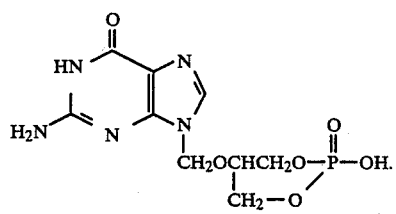

5. A compound of Formula I of claim 1 wherein $OR^1$ and $OR^2$ together are

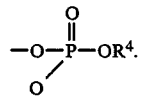

6. A compound of Formula II of claim 1 wherein $OR^1$ and $OR^2$ together are

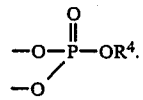

7. A method of treating a virus infection in a mammalian or avian or piscine species comprising administering a compound of claim 1, in a quantity effective to impart an anti-viral effect.

8. A method according to claim 7 wherein the virus is a herpes virus.

9. A method according to claim 7 wherein the compound is administered at from about 0.01 to about 200 mg/kg.

10. A method according to claim 7 wherein the compound is administered topically at a dosage level of from about 0.1% to about 5% by weight.

11. A method according to claim 10 wherein the dosage level is from about 0.25% to about 3% by weight.

12. A method according to claim 7 wherein the compound is administered orally or parenterally, at a dosage level of from about 0.8 to about 100 mg/kg.

13. A method according to claim 12 wherein the dosage level is from about 5 to about 50 mg/kg.

14. A pharmaceutical composition comprising an amount of a compound of claim 1 effective to impart an anti-viral effect and a pharmaceutically acceptable carrier.

15. A method according to claim 14 wherein the virus is a herpes virus.

* * * * *